United States Patent
Richard et al.

(10) Patent No.: US 9,162,976 B2
(45) Date of Patent: Oct. 20, 2015

(54) COMPOSITION CONTAINING A DIBENZOYLMETHANE SCREENING AGENT AND A HYDROPHILIC OR WATER-SOLUBLE MEROCYANIN UV-SCREENING AGENT; PROCESS FOR PHOTOSTABILIZING THE DIBENZOYLMETHANE SCREENING AGENT

(75) Inventors: Herve Richard, Gagny (FR); Benoit Muller, Paris (FR)

(73) Assignee: L'OREAL, Paris (FR)

( * ) Notice: Subject to any disclaimer, the term of this patent is extended or adjusted under 35 U.S.C. 154(b) by 3 days.

(21) Appl. No.: 13/634,194

(22) PCT Filed: Mar. 7, 2011

(86) PCT No.: PCT/EP2011/053376
§ 371 (c)(1),
(2), (4) Date: Nov. 16, 2012

(87) PCT Pub. No.: WO2011/113718
PCT Pub. Date: Sep. 22, 2011

(65) Prior Publication Data
US 2013/0058990 A1  Mar. 7, 2013

Related U.S. Application Data

(60) Provisional application No. 61/282,733, filed on Mar. 24, 2010.

(30) Foreign Application Priority Data

Mar. 15, 2010 (FR) ..................... 10 51823
Oct. 22, 2010 (FR) ..................... 10 58690
Nov. 25, 2010 (FR) ..................... 10 59756

(51) Int. Cl.
*A61K 8/49* (2006.01)
*A61K 8/11* (2006.01)
*A61K 8/42* (2006.01)
*A61K 8/44* (2006.01)
*A61K 8/46* (2006.01)
*A61Q 17/04* (2006.01)
*C07C 229/46* (2006.01)
*C07C 309/18* (2006.01)
*C07C 317/48* (2006.01)
*C07D 211/46* (2006.01)
*C07D 277/04* (2006.01)
*C07C 309/15* (2006.01)
*A61K 8/35* (2006.01)
*A61K 8/40* (2006.01)
(Continued)

(52) U.S. Cl.
CPC ............... *C07C 309/15* (2013.01); *A61K 8/35* (2013.01); *A61K 8/40* (2013.01); *A61K 8/44* (2013.01); *A61K 8/466* (2013.01); *A61K 8/49* (2013.01); *A61K 8/4926* (2013.01); *A61Q 17/04* (2013.01); *C07C 229/30* (2013.01); *C07C 229/46* (2013.01); *C07C 255/30* (2013.01); *C07C 255/31* (2013.01); *C07C 309/12* (2013.01); *C07C 309/14* (2013.01); *C07C 309/22* (2013.01); *C07C 309/23* (2013.01); *C07D 211/46* (2013.01); *C07D 263/14* (2013.01); *C07D 277/10* (2013.01); *C07C 2101/16* (2013.01)

(58) Field of Classification Search
CPC ...... A61K 8/466; A61Q 17/04; C07C 229/30; C07C 229/46; C07C 309/12; C07C 309/14; C07C 309/15; C07C 309/22
See application file for complete search history.

(56) References Cited

U.S. PATENT DOCUMENTS

| 4,195,999 | A * | 4/1980 | Adachi et al. | 430/507 |
| 4,443,534 | A * | 4/1984 | Kojima et al. | 430/512 |
| 2005/0255055 | A1 * | 11/2005 | Wagner et al. | 424/59 |
| 2006/0204457 | A1 * | 9/2006 | Toda et al. | 424/59 |

FOREIGN PATENT DOCUMENTS

| GB | 2 416 351 A | 1/2006 |
| WO | WO-2004/006878 A1 | 1/2004 |

(Continued)

*Primary Examiner* — Suzanne Ziska
*Assistant Examiner* — Thurman Wheeler
(74) *Attorney, Agent, or Firm* — Novak Druce Connolly Bove + Quigg LLP

(57) ABSTRACT

The present invention relates to a cosmetic composition containing a combination i) of at least one screening agent of the dibenzoylmethane derivative type and ii) of at least one particular hydrophilic or water-soluble merocyanin UV-screening agent, especially corresponding to one of the formulae (I) or (II) below:

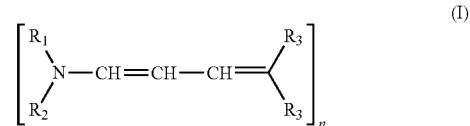

(I)

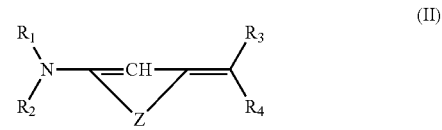

(II)

in which at least one or two of the radicals contain: either an alkylsulfonate radical in its acid or salified form, or one or two hydroxyl radicals. The invention also relates to a process for the radiation-photostabilization of at least one screening agent of the dibenzoylmethane derivative type with an effective amount of at least one particular hydrophilic or water-soluble merocyanin UV-screening agent, especially corresponding to one of the formulae (I) or (II).

6 Claims, No Drawings

(51) Int. Cl.
  *C07C 229/30*  (2006.01)
  *C07C 255/30*  (2006.01)
  *C07C 255/31*  (2006.01)
  *C07C 309/12*  (2006.01)
  *C07C 309/14*  (2006.01)
  *C07C 309/22*  (2006.01)
  *C07C 309/23*  (2006.01)
  *C07D 263/14*  (2006.01)
  *C07D 277/10*  (2006.01)

(56) References Cited

FOREIGN PATENT DOCUMENTS

| WO | WO-2004/075871 A1 | 9/2004 |
| WO | WO-2006/125676 A1 | 11/2006 |
| WO | WO-2007/014848 A2 | 2/2007 |
| WO | WO-2008/080645 A1 | 7/2008 |
| WO | WO-2008/090066 A2 | 7/2008 |

* cited by examiner

COMPOSITION CONTAINING A DIBENZOYLMETHANE SCREENING AGENT AND A HYDROPHILIC OR WATER-SOLUBLE MEROCYANIN UV-SCREENING AGENT; PROCESS FOR PHOTOSTABILIZING THE DIBENZOYLMETHANE SCREENING AGENT

CROSS REFERENCE TO RELATED APPLICATIONS

This application is a National Phase filing under 35 U.S.C. §371 of PCT/EP2011/053376 filed on Mar. 7, 2011; and this application claims priority to Application No. 1051823 filed in France on Mar. 15, 2010 under 35 U.S.C. §119, and this application claims priority to Application No. 1058690 filed in Oct. 22, 2010 on France under 35 U.S.C. §119, and this application claims priority to Application No. 1059756 filed in France on Nov. 25, 2010 under 35 U.S.C. §119; and this application claims the benefit of U.S. Provisional Application No. 61/282,733 filed on Mar. 24, 2010; the entire contents of each application is hereby incorporated by reference.

The present invention relates to a cosmetic composition containing a combination i) of at least one screening agent of the dibenzoylmethane derivative type and ii) of at least one particular hydrophilic or water-soluble merocyanin UV-screening agent, the definition of which will be given below.

The invention also relates to a process for the radiation-photostabilization of at least one screening agent of the dibenzoylmethane derivative type with an effective amount of at least one particular hydrophilic or water-soluble merocyanin UV-screening agent, the definition of which will be given below.

It is known that light radiation with wavelengths of between 280 nm and 400 nm permits tanning of the human epidermis and that light rays with wavelengths more particularly between 280 and 320 nm, known as UV-B rays, cause skin burns and erythema which can harm the development of a natural tan. For these reasons, and also for aesthetic reasons, there is constant demand for means for controlling this natural tanning in order thus to control the colour of the skin; this UV-B radiation should thus be screened out.

It is also known that UV-A rays, with wavelengths between 320 and 400 nm, which cause tanning of the skin, are liable to induce adverse changes therein, in particular in the case of sensitive skin or skin that is continually exposed to solar radiation. UV-A rays cause in particular a loss of elasticity of the skin and the appearance of wrinkles leading to premature ageing of the skin. They promote triggering of the erythemal reaction or amplify this reaction in certain individuals and may even be the cause of phototoxic or photoallergic reactions. Thus, for aesthetic and cosmetic reasons, for instance conservation of the skin's natural elasticity, people increasingly wish to control the effect of UV-A rays on their skin. It is thus desirable also to screen out UV-A radiation.

For the purpose of protecting the skin and keratin materials against UV radiation, antisun compositions comprising organic screening agents that are active in the UV-A range and in the UV-B range are generally used. The majority of these screening agents are liposoluble.

In this respect, one particularly advantageous family of UV-A screening agents currently consists of dibenzoylmethane derivatives, and in particular 4-tert-butyl-4'-methoxydibenzoylmethane, which have high intrinsic absorbing power. These dibenzoylmethane derivatives, which are products that are now well known per se as screening agents that are active in the UV-A range, are described in particular in French patent applications FR-A-2 326 405 and FR-A-2 440 933, and also in European patent application EP-A-0 114 607; 4-tert-butyl-4'-methoxy-dibenzoylmethane is moreover currently sold under the trade name Parsol 1789® by the company DSM Nutritional Products.

Unfortunately, it has been found that dibenzoyl-methane derivatives are products that are relatively sensitive to ultraviolet radiation (especially UV-A), i.e., more specifically, they have an annoying tendency to be degraded more or less quickly under the action of this radiation. Thus, this substantial lack of photochemical stability of dibenzoylmethane derivatives towards ultraviolet radiation, to which they are by nature intended to be subjected, does not make it possible to ensure constant protection during prolonged exposure to the sun, and so the user must make repeated applications at regular and close time intervals in order to obtain effective protection of the skin against UV rays.

Patent application WO 01/28732 discloses a process for photostabilizing a dibenzoylmethane derivative with a merocyanin phenyl sulfone derivative. Firstly, this photostabilization of the dibenzoylmethane derivative with the merocyanin phenyl sulfone derivative is not entirely satisfactory. Secondly, these merocyanin phenyl sulfone derivatives have the drawback of being degraded in the presence of dibenzoylmethane under the influence of UV radiation.

Patent application WO 2008/090 066 has already proposed photostabilizing dibenzoylmethane derivatives with cyclic merocyanin cyanoacetate derivatives. In this case also, the photostabilization of the dibenzoylmethane derivative remains insufficient and these merocyanin cyanoacetate derivatives also have the drawback of being degraded in the presence of dibenzoylmethane.

The photostabilization of dibenzoylmethane derivatives towards UV radiation thus constitutes, at the present time, a problem that has still not been solved entirely satisfactorily.

The Applicant has now discovered, surprisingly, that by combining the dibenzoylmethane derivatives mentioned above with a particular hydrophilic or water-soluble merocyanin UV-screening agent, the definition of which will be given later, which are active in the UV-A range, it is possible firstly to substantially improve the photochemical stability (or photostability) of the dibenzoylmethane derivatives and, secondly, to extend the filtration of the composition in the longer UV-A range while at the same time giving cosmetically acceptable coloration.

This discovery forms the basis of the present invention.

Thus, in accordance with one of the subjects of the present invention, a composition is now proposed comprising, in a cosmetically acceptable support, at least one UV-screening system, characterized in that it comprises:
(i) at least one dibenzoylmethane derivative and
(ii) at least one particular hydrophilic or water-soluble merocyanin UV-screening agent, the definition of which will be given below.

Another subject of the invention also concerns a process for improving the chemical stability towards UV radiation of at least one dibenzoylmethane derivative, which consists in combining the said dibenzoylmethane derivative with an effective amount of at least one particular hydrophilic or water-soluble merocyanin UV-screening agent, the definition of which will be given below.

Other characteristics, aspects and advantages of the invention will emerge on reading the detailed description that follows.

The term "cosmetically acceptable" means compatible with the skin and/or its integuments, which has a pleasant colour, odour and feel, and which does not cause any unacceptable discomfort (stinging, tautness or redness) liable to dissuade the consumer from using this composition.

In the rest of the present description, the term "hydrophilic UV-screening agent" means any agent for screening out UV radiation, which may be soluble in an aqueous phase at 1-5% by weight (transparent) or water-dispersible in the form of a suspension of particles smaller than 100 microns.

Also, the term "water-soluble screening agent" means any agent for screening out UV radiation, which may be soluble in its cosmetically acceptable salt form in an aqueous phase at more than 5% by weight.

The term "effective amount" means an amount that is sufficient to obtain a notable and significant improvement in the photostability of the dibenzoylmethane derivative(s) in the cosmetic composition. This minimum amount of merocyanin derivatives according to the invention, which may vary according to the nature of the support adopted for the composition, may be determined without any difficulty by means of a standard test for measuring photostability, such as the test given in the examples hereinbelow.

Among the dibenzoylmethane derivatives that may especially be mentioned, in a non-limiting manner, are:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methxydibenzoylmethane,
2,4-dimethyl-4'-methoxydibenzoylmethane,
2,6-dimethyl-4-tert-butyl-4'-methoxydibenzoylmethane.

Among the dibenzoylmethane derivatives mentioned above, 4-isopropyldibenzoylmethane will be used in particular, which is sold under the name Eusolex 8020 by the company Merck, and corresponds to the following formula:

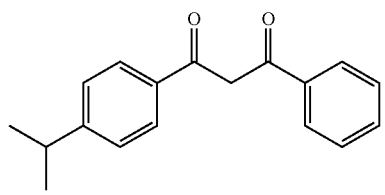 [SMILES: CC(C)c1ccc(C(=O)CC(=O)c2ccccc2)cc1]

It is most particularly preferred to use 4-(tert-butyl)-4'-methoxydibenzoylmethane or Butyl Methoxy Dibenzoylmethane or Avobenzone, sold under the trade name Parsol 1789 by the company DSM Nutritional Products, Inc.; this screening agent corresponds to the following formula:

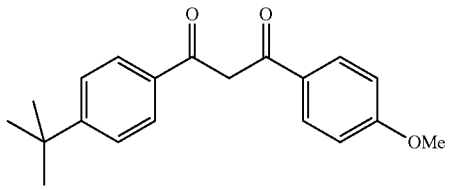 [SMILES: COc1ccc(C(=O)CC(=O)c2ccc(C(C)(C)C)cc2)cc1]

The dibenzoylmethane derivative(s) may be present in the compositions in accordance with the invention in contents preferably ranging from 0.01% to 20% by weight, more preferentially from 0.1% to 10% by weight and even more preferentially from 0.1% to 6% by weight relative to the total weight of the composition.

The hydrophilic or water-soluble merocyanin compounds in accordance with the invention are chosen from the group formed by:
(1) those corresponding to one of the formulae (I) and (II) below, and the salts thereof:

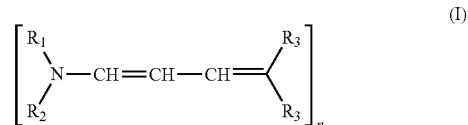

(I)

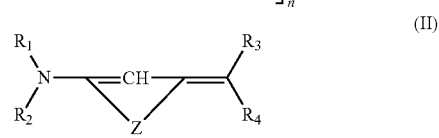

(II)

in which:
$R_1$ and $R_2$, which may be identical or different, represent H; a linear or branched $C_1$-$C_{22}$ alkyl radical possibly containing from 1 to 3 oxygen atoms; a $C_3$-$C_8$ cycloalkyl radical, which is unsubstituted or substituted with $C_1$-$C_4$ alkyl radicals; the said radicals $R_1$ and $R_2$ possibly containing an alkylsulfonate radical in its acid or salified form or one or two hydroxyl radicals;
$R_1$ and $R_2$ may form, together with the nitrogen, a ring containing the group —$(CH_2)_m$—, which is uninterrupted or interrupted with one or more —O—, —S— or —NH—,
$R_1$ may form, with the carbon alpha to the nitrogen, a ring containing the group —$(CH_2)_m$—, which is uninterrupted or interrupted with one or more —O—, —S— or —NH—,
$R_3$ represents a carboxyl, —$COOR_5$, —$CONHR_5$, —$COR_5$, —$CONR_5R_1$, $SO_2R_5$, or —CN group,
$R_4$ represents a carboxyl, —$COOR_6$, —$CONHR_6$, —$COR_E$, —$CONR_6R_2$ or $SO_2R_6$ group,
$R_5$ and $R_6$, which may be identical or different, represent a linear or branched $C_1$-$C_{22}$ alkyl radical possibly containing from 1 to 3 oxygen atoms; a $C_3$-$C_8$ cycloalkyl radical, which is unsubstituted or substituted with $C_1$-$C_4$ alkyl radicals;
the said radicals $R_5$ and $R_6$ possibly containing an alkylsulfonate radical in its acid or salified form or one or two hydroxyl radicals,
Z represents the group —$(CH_2)_t$—, which is uninterrupted or interrupted with —O—, —S— or —$NR_7$—, and/or unsubstituted or substituted with one or two $C_1$-$C_6$ alkyl radicals,
$R_7$ is a $C_1$-$C_5$ alkyl radical possibly containing an alkylsulfonate radical in its acid or salified form or one or two hydroxyl radicals,
n is 1-2; -m is 1-7; -l is 1-4;
with at least one or two of the radicals $R_1$, $R_2$, $R_5$, $R_6$ and $R_7$ containing
either an alkylsulfonate radical in its acid or salified form or one or two hydroxyl radicals;
with the proviso that:
(i) when n=2, one of the radicals $R_1$, $R_5$ or $R_6$ is an alkyl diradical or $R_1$ and $R_2$ together with two nitrogen atoms form a cyclic divalent radical —$(CH_2)_m$—;
(ii) $R_1$ and $R_2$ are not simultaneously a hydrogen atom;
(iii) when $R_3$ is —CN, then at least one of the radicals $R_1$, $R_2$ or $R_6$ must contain an alkylsulfonate group in its acid or salified form;
(2) the merocyanin compounds chosen from the group formed by the following molecules, and also salts thereof and the E,E-, E,Z- or Z,Z-geometrical isomer forms thereof

5
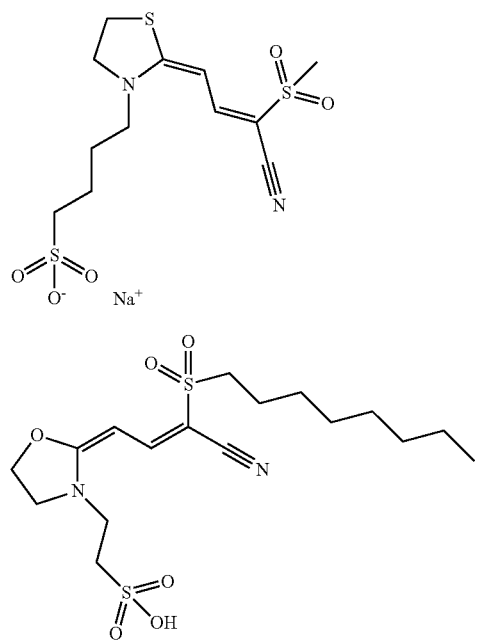
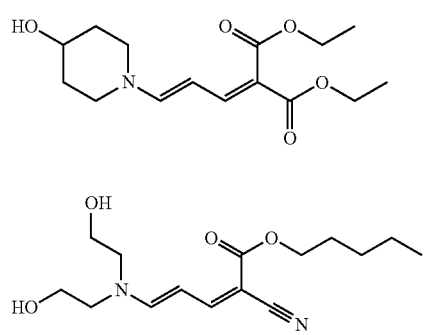
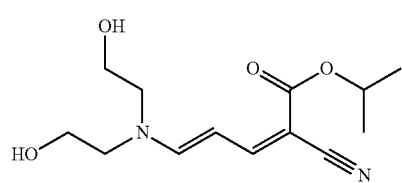
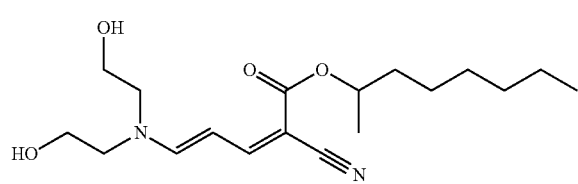
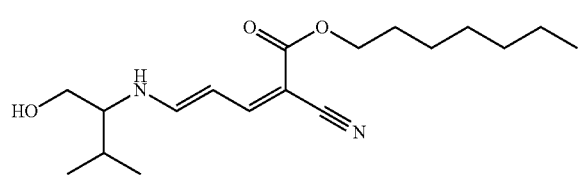
6
(v) 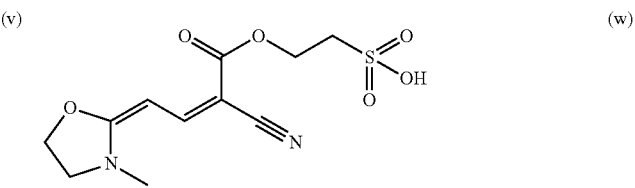 (w)
(x) 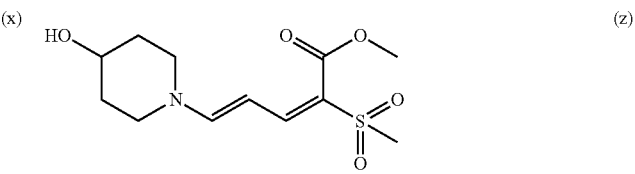 (z)
(ag) 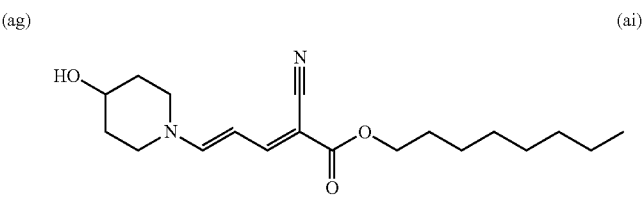 (ai)
(aj) 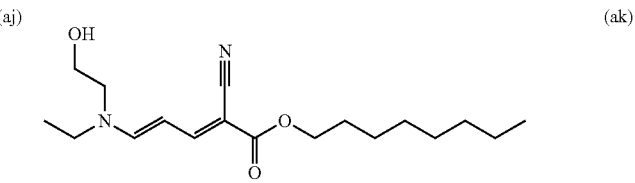 (ak)
(al) 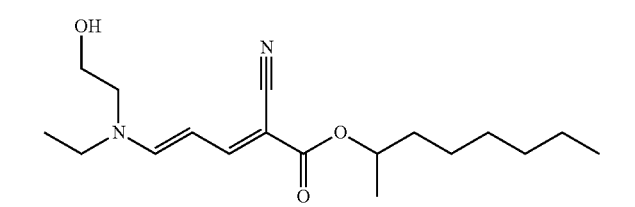 (am)
(an) 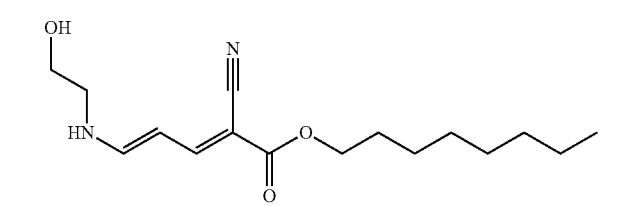 (ao)
(ap) 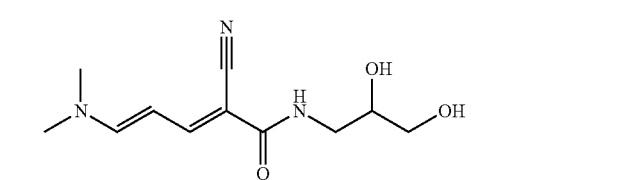 (aq)

-continued
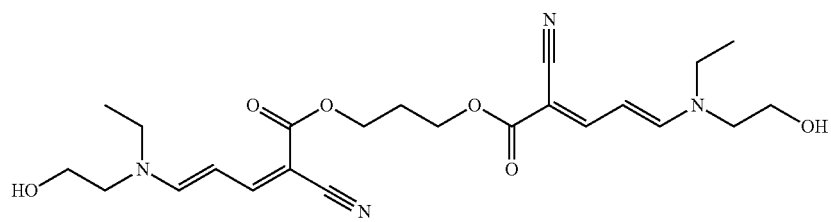
(ar)
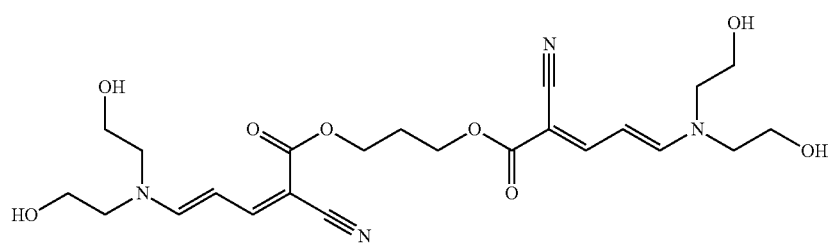
(as)
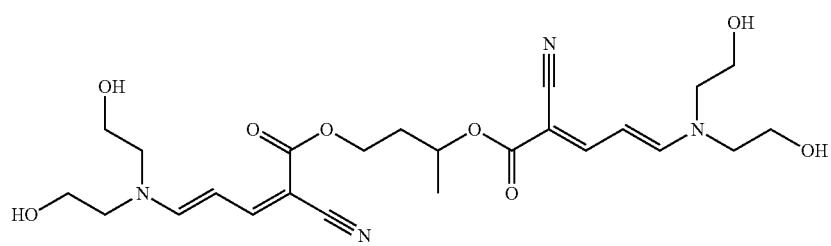
(at)
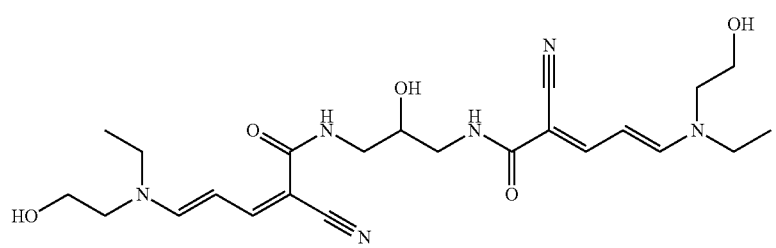
(au)
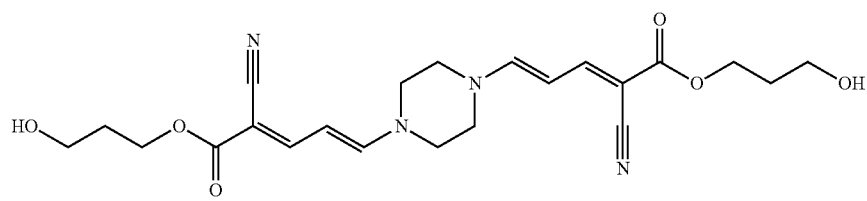
(av)
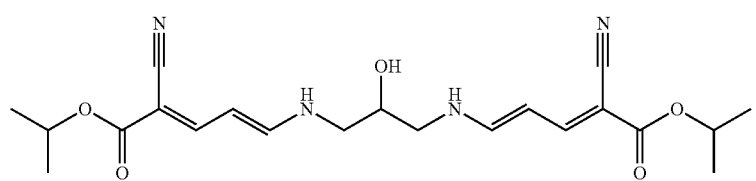
(aw)
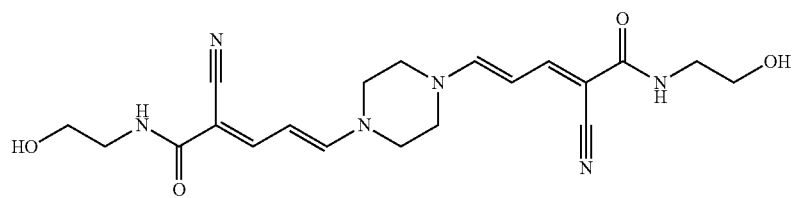
(ax)

-continued
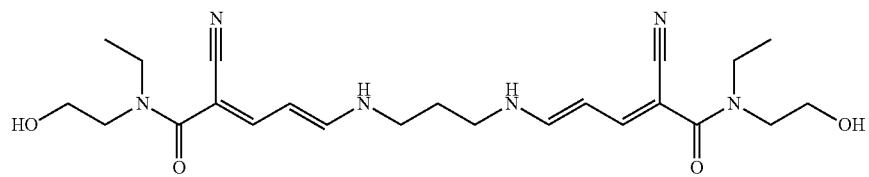
(ay)
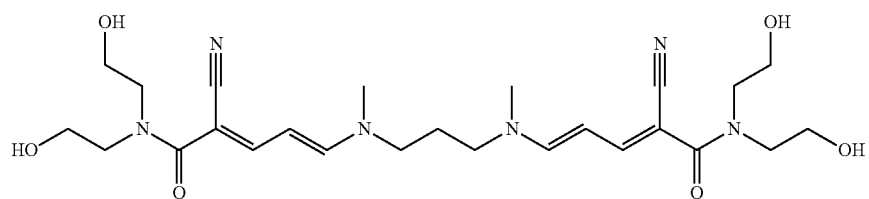
(az)
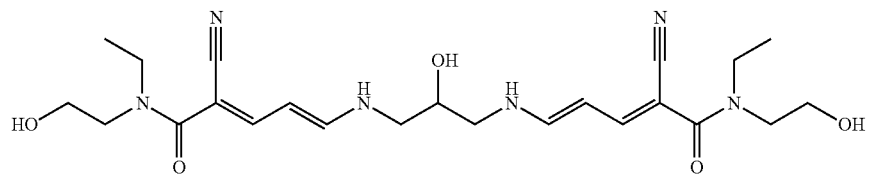
(ba)
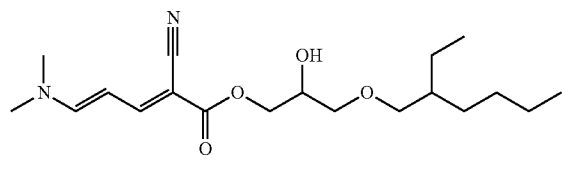
(bb)
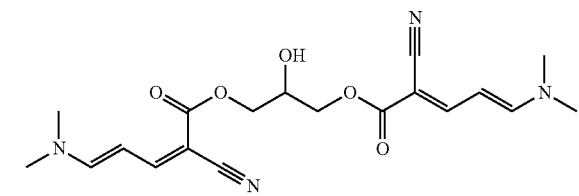
(bc)
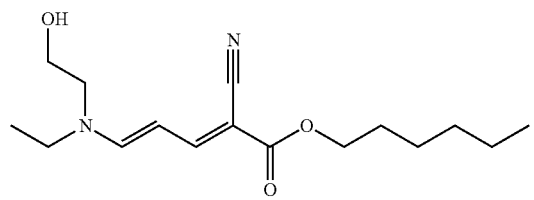
(bd)
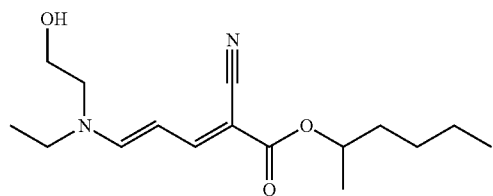
(be)
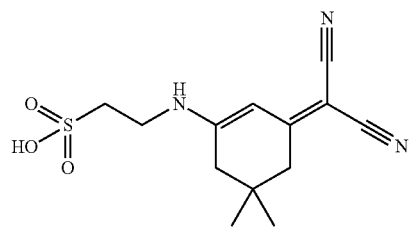
(bf)
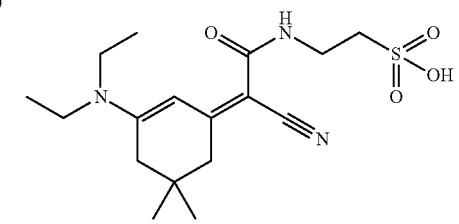
(bi)
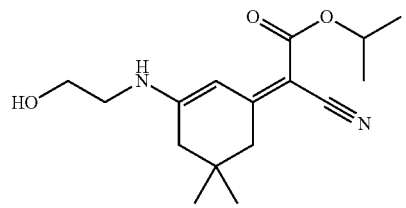
(bl)
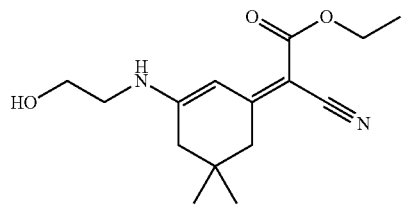
(bm)

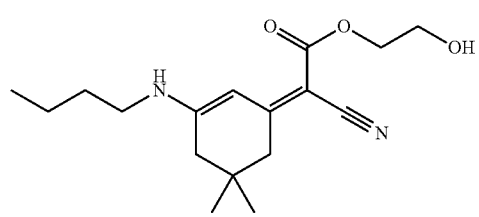
(bn)

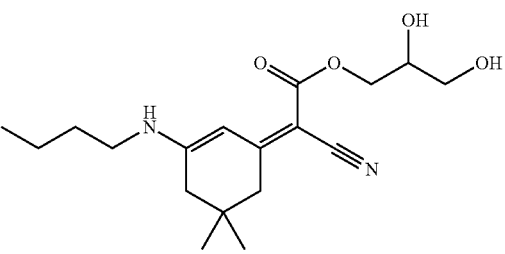
(bo)

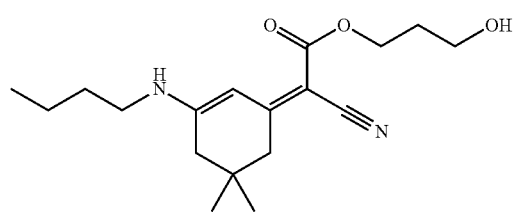
(bp)

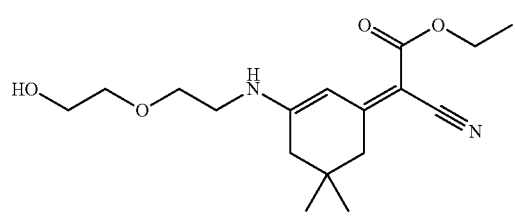
(bq)

The merocyanin compounds of the invention may be in the E,E-, E,Z- or Z,Z-geometrical isomer forms.

The term "diradical" means a divalent radical such that the two units

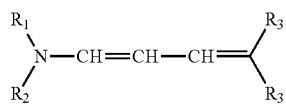

are linked together via this diradical.

Illustrations that may be mentioned include compounds (u) and (ar) below:

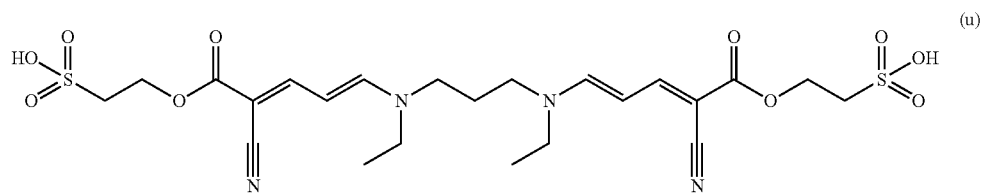
(u)

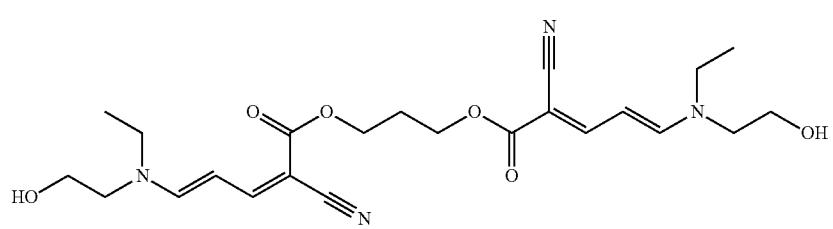
(ar)

In the case where n=2, for instance a cyclic divalent radical —$(CH_2)_m$— formed by $R_1$ and $R_2$ with the two nitrogen atoms, mention may be made of the compound (ax)

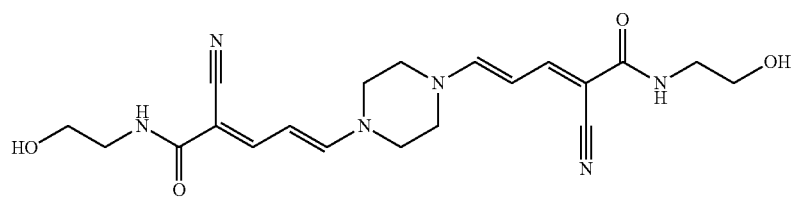
(ax)

Examples of linear or branched alkyl radicals that may be mentioned include: methyl, ethyl, n-propyl, isopropyl, 1-methylethyl, butyl, pentyl, hexyl, 2-ethylhexyl, octyl, 1-methylheptyl.

$C_3$-$C_8$ cycloalkyl radicals that may be mentioned include cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-methyl-1-butylcyclopropyl, 1,2-dimethylcyclypropyl, 1-methyl-2-ethylcyclopropyl and cyclooctyl.

The acceptable salts of the merocyanin compounds described in the present invention comprise conventional non-toxic salts of the said compounds, such as those formed from organic or mineral bases, such as amine salts, for instance salts of alkanolamines such as triethanolamine, amino acid salts or aminopropanediol salts, and salts of an alkali metal or alkaline-earth metal, for instance sodium or potassium.

The preferred salts are salts of an alkali metal such as sodium or potassium, or salts of an amine such as triethanolamine.

The preferred compounds of formula (I) are those for which the following conditions are satisfied:

$R_1$ denotes hydrogen; a linear or branched $C_1$-$C_8$ alkyl radical possibly containing from 1 to 3 oxygen atoms, $R_2$ denotes a linear or branched $C_1$-$C_8$ alkyl radical possibly containing from 1 to 3 oxygen atoms or a $C_5$-$C_6$ cycloalkyl radical, $R_3$ denotes a group —COOR$_S$, —CN or —CONHR$_5$, $R_4$ denotes a group —COOR$_6$, —CONHR$_6$ or —SO$_2$R$_6$, $R_5$ denotes a linear or branched $C_1$-$C_{12}$ alkyl radical possibly containing from 1 to 3 oxygen atoms, n is equal to 1 or 2;

with at least one or two of the radicals $R_1$, $R_2$, $R_5$, $R_6$ containing either an alkylsulfonate radical in its acid or salified form or one or two hydroxyl radicals.

The compounds of formula (I) with one or two alkylsulfonate radicals that are even more particularly preferred are chosen from those having the following formulae:

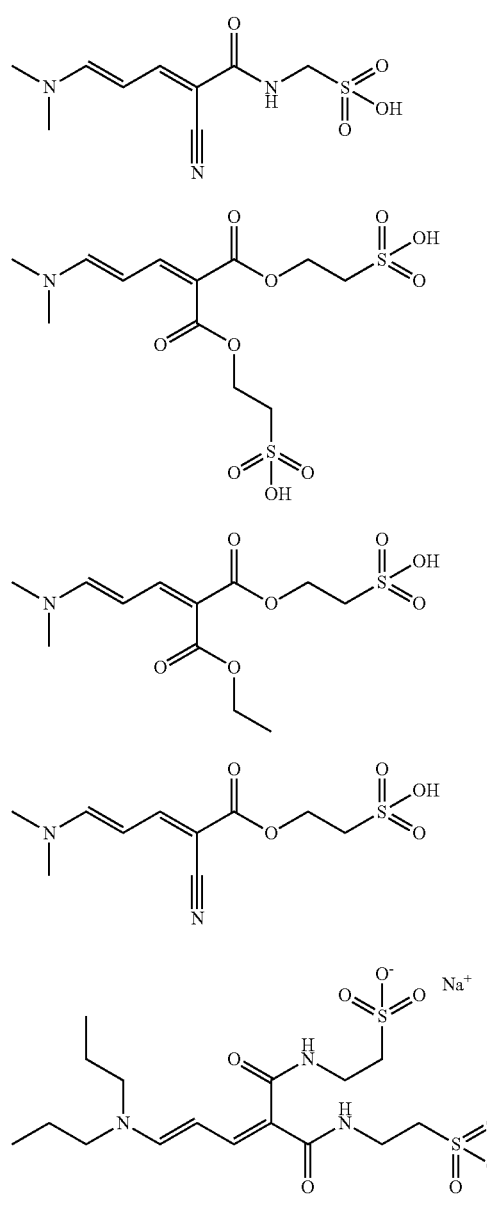
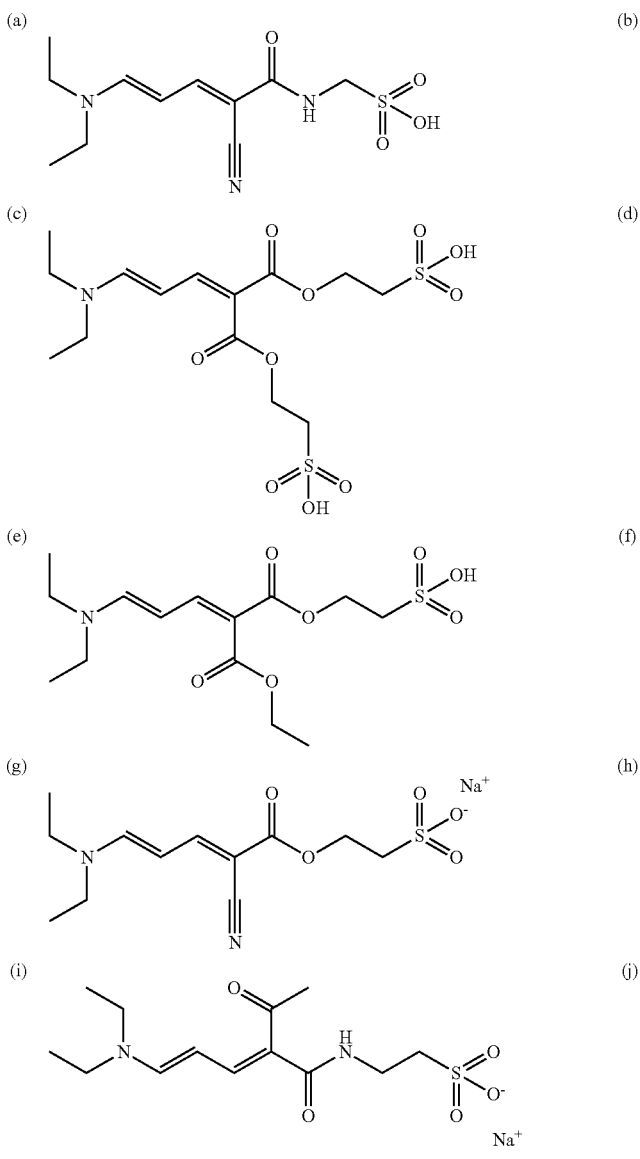

-continued
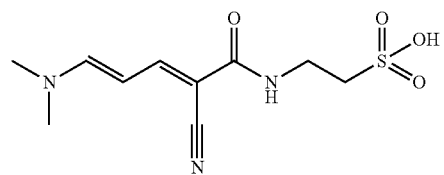 (k)
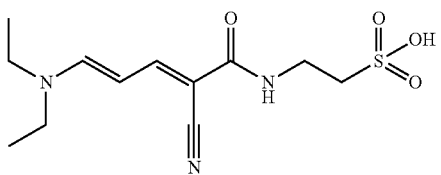 (l)
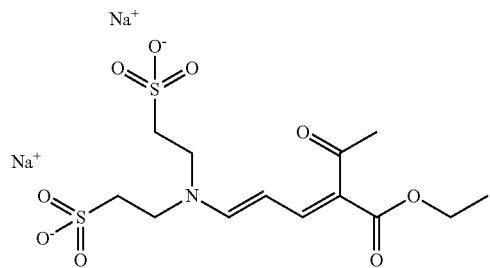 (m)
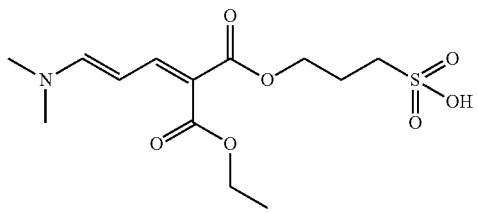 (n)
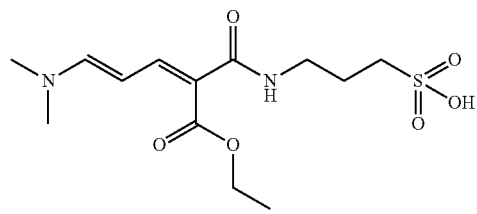 (o)
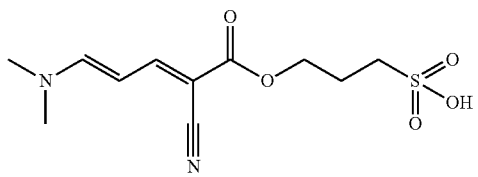 (p)
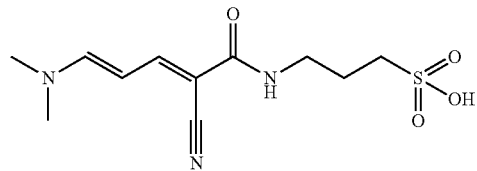 (q)
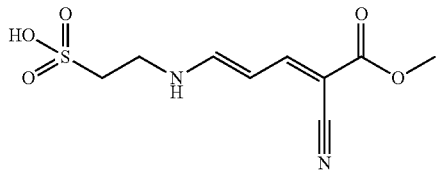 (r)
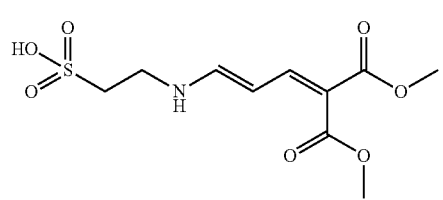 (s)
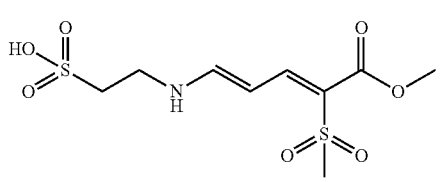 (t)
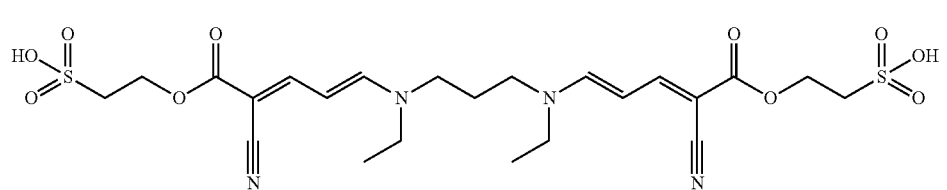 (u)

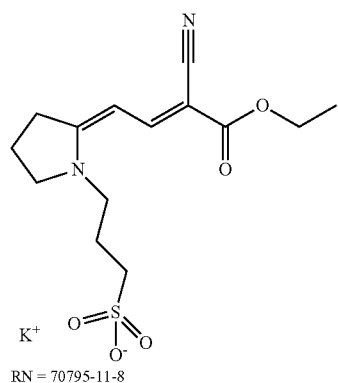
RN = 70795-11-8

The compounds of formula (I) containing hydroxyl groups that are particularly preferred are those having the following formulae:

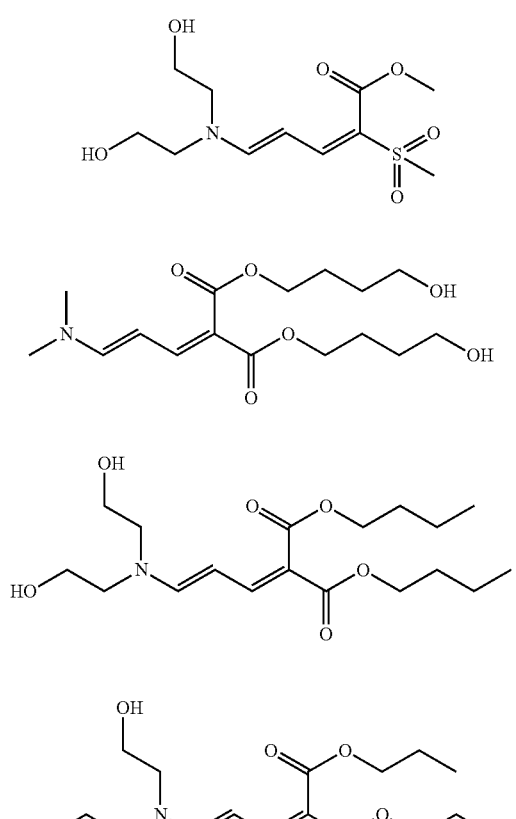

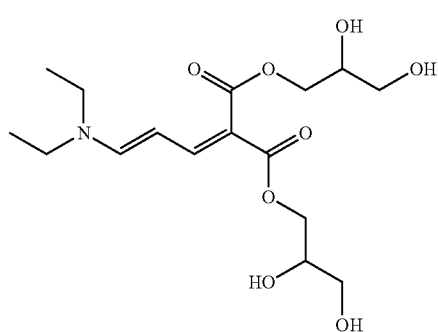

The preferred compounds of formula (II) are those for which the following conditions are satisfied:

$R_1$ denotes hydrogen; a linear or branched $C_1$-$C_{10}$ alkyl radical possibly containing from 1 to 3 oxygen atoms, $R_2$ denotes a linear or branched $C_1$-$C_{10}$ alkyl radical possibly containing from 1 to 3 oxygen atoms; a $C_5$-$C_6$ cycloalkyl, $R_3$ denotes a group —$COOR_5$ or CN, $R_4$ denotes a group —$COOR_6$ or —$SO_2R_6$, $R_5$ denotes a linear or branched $C_1$-$C_{12}$ alkyl radical possibly containing from 1 to 3 oxygen atoms, Z is —$(CH_2)_3$— which may or may not be substituted with two groups $CH_3$, n is equal to 1 or 2;

with at least one or two of the radicals $R_1$, $R_2$, $R_5$, $R_6$ containing
either an alkylsulfonate radical in its acid or salified form
or one or two hydroxyl radicals.

The compounds of formula (II) that are particularly preferred are those having the following formulae:

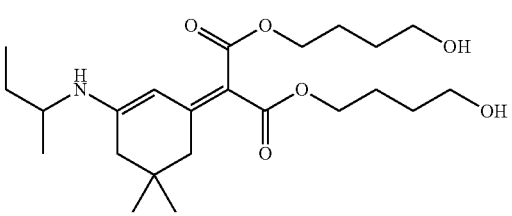

-continued
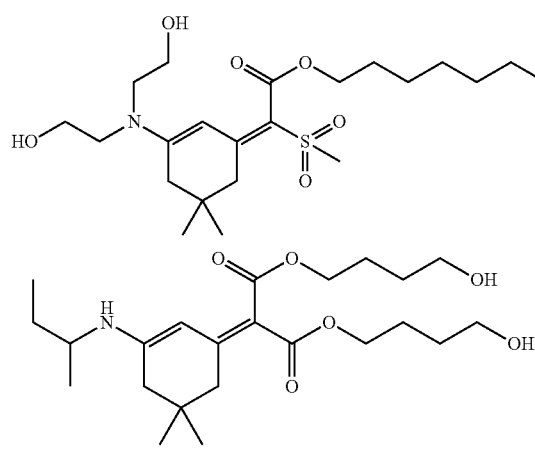
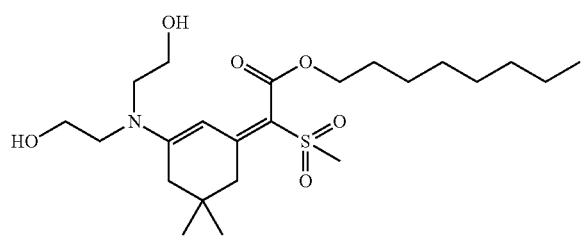
Among the merocyanin compounds in accordance with the invention that are particularly preferred, the following compounds will be chosen more particularly:
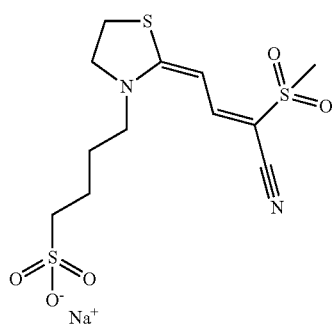
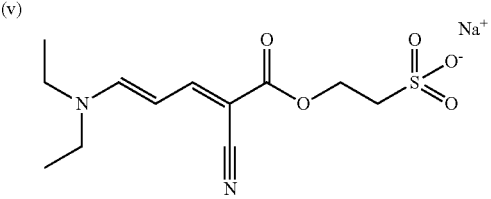
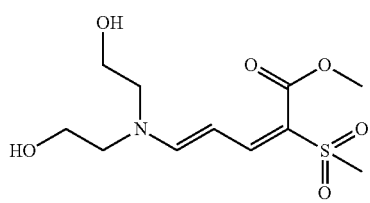
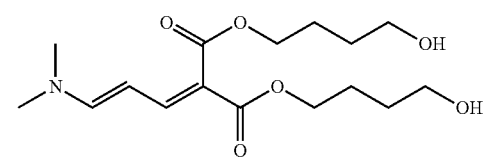
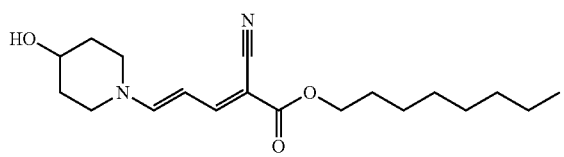
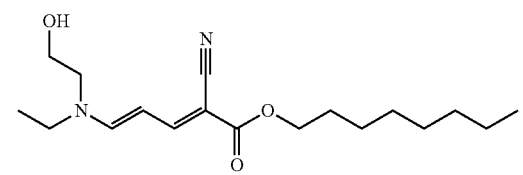
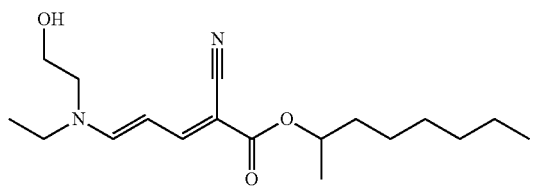
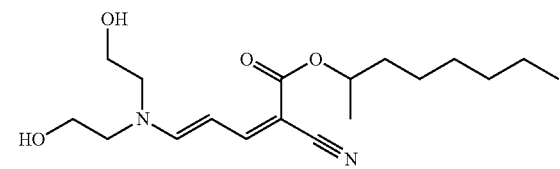

-continued
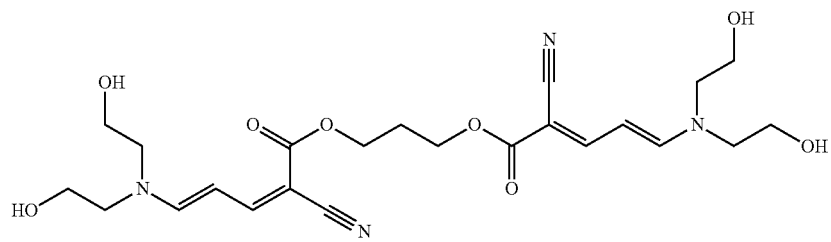
(as)
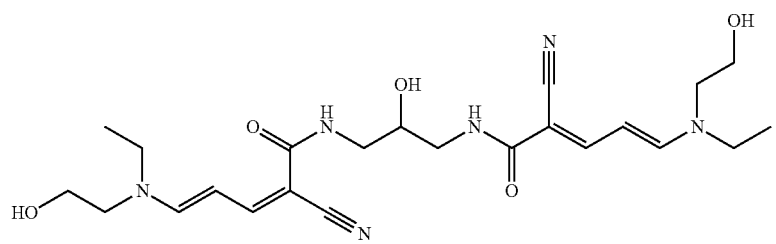
(au)
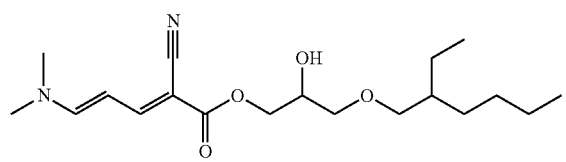
(bb)
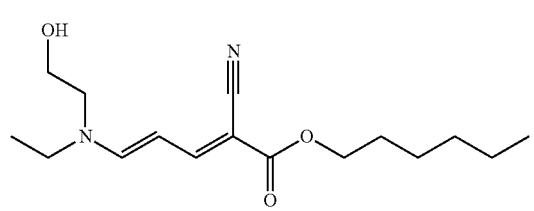
(bc)
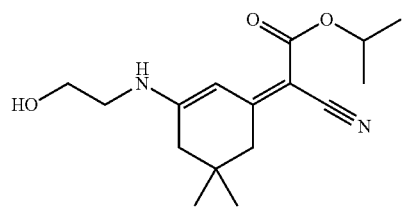
(bd)
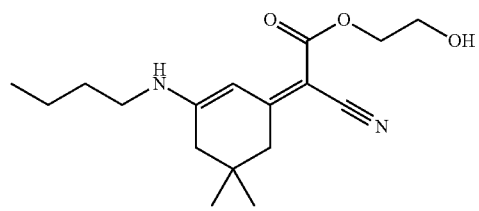
(be)
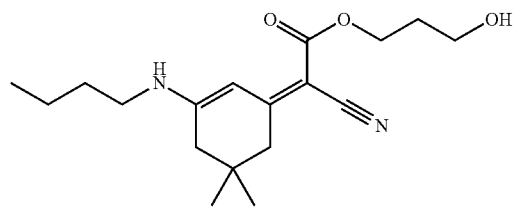
(bl)
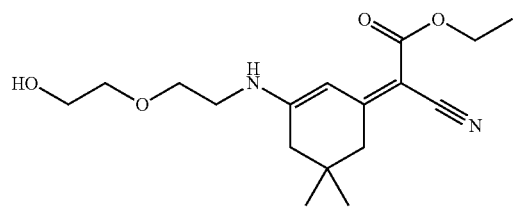
(bm)
(bn)
(bo)
(bp)
(bq)

The linear merocyanin derivatives in accordance with the invention, in particular those of formula (I), may be prepared according to a method described in U.S. Pat. Nos. 4,045,229, 4,195,999 and US 2009/0 170 008 according to the following scheme (route 1):

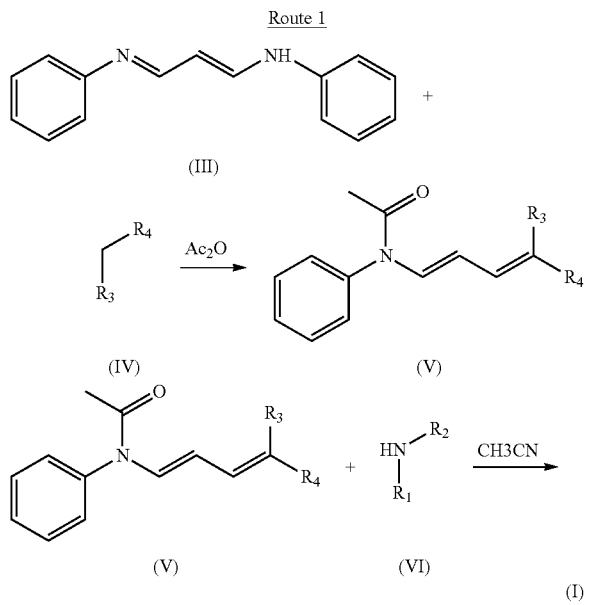

or according to a method described in patent WO 00/07989, and according to the following scheme (route 2):

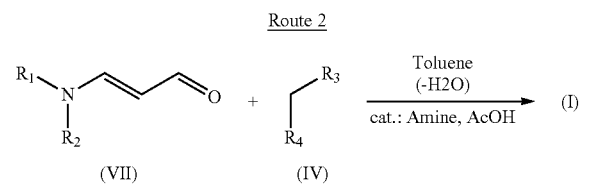

in which the radicals $R_1$, $R_2$, $R_3$ and $R_4$ have the meaning of formula (I).

The cyclic merocyanin derivatives in accordance with the invention, in particular those of formula (II), may be prepared according to a method described in IP.COM Journal 9(5A), 29-30 (2009) according to the following scheme:

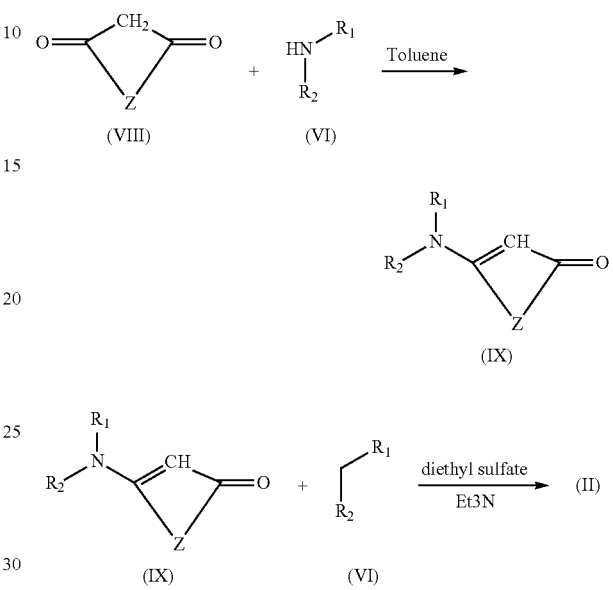

in which the radicals $R_1$, $R_2$, $R_3$, $R_4$ and Z have the meaning of formula (II).

Some of the hydrophilic or water-soluble merocyanin compounds in accordance with the invention are novel and constitute another subject of the invention.

Among the compounds of formula (I) with one or two alkylsulfonate radicals, the following compounds are novel:

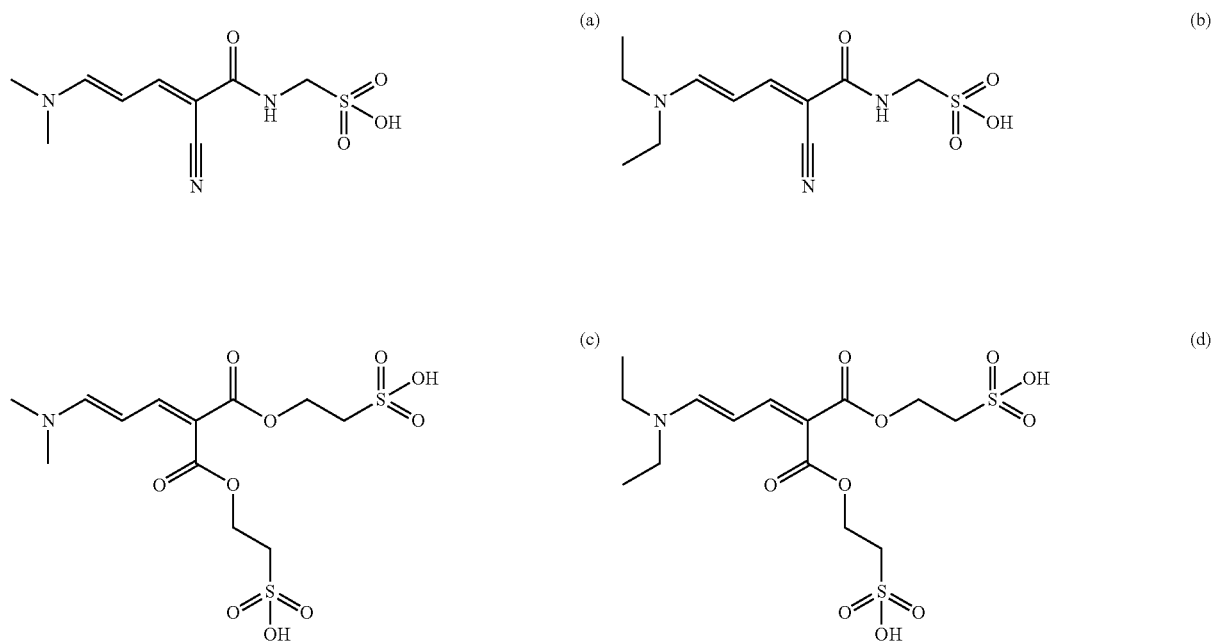

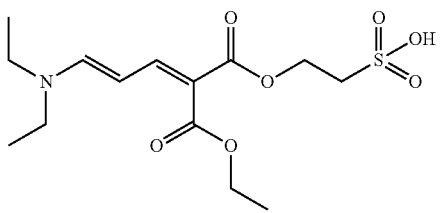
(e)
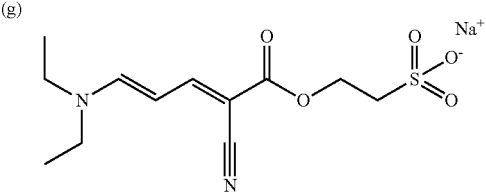
(g)
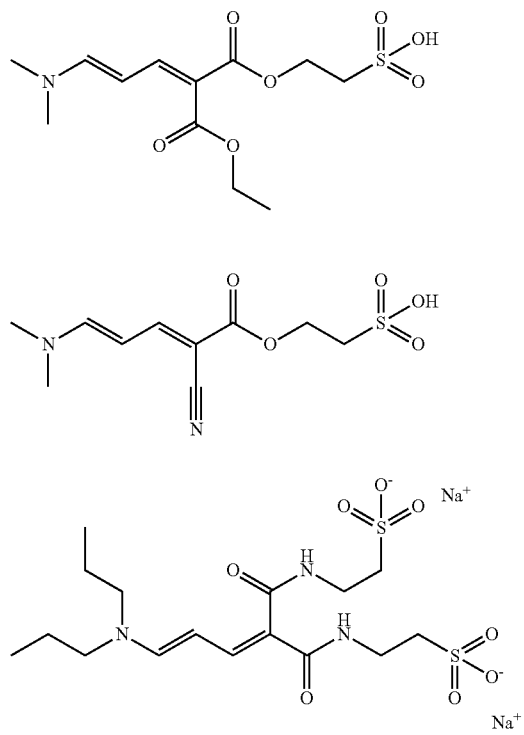
(f)
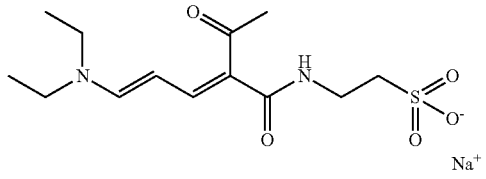
(i)
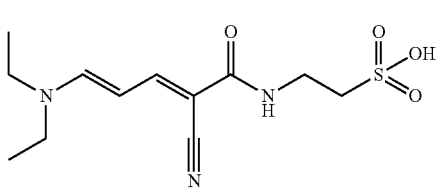
(k)
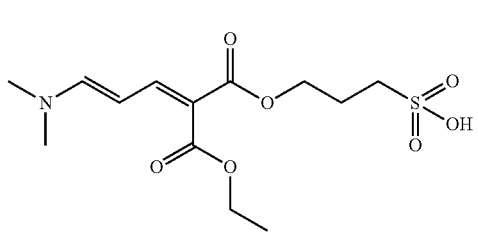
(m)
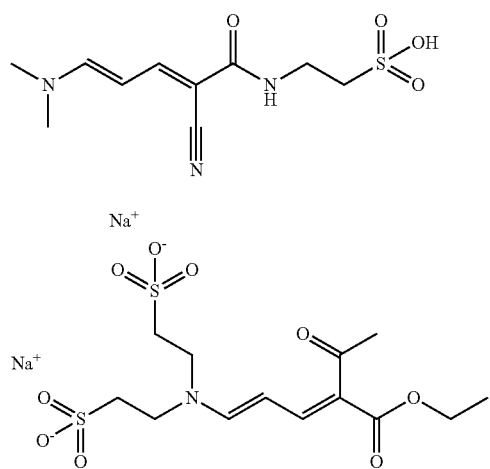
(o)
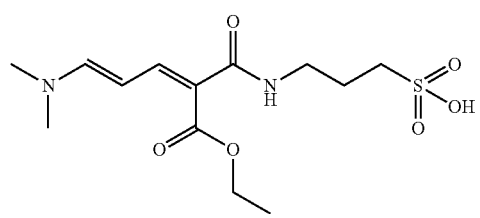
(q)
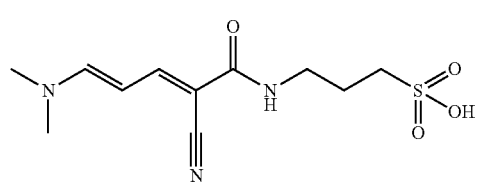
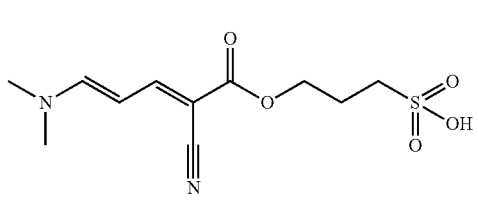
(n)
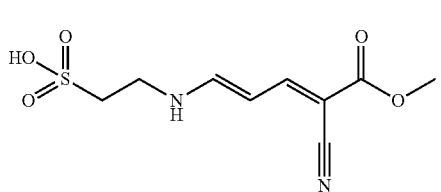
(p)
(r)

(s) 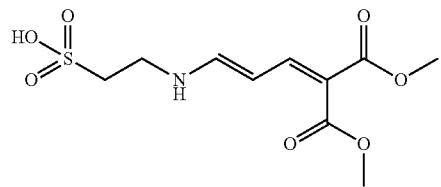
(t) 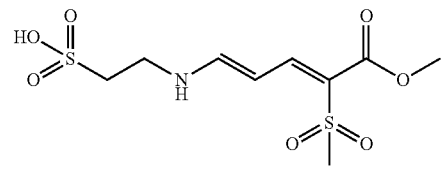
(u) 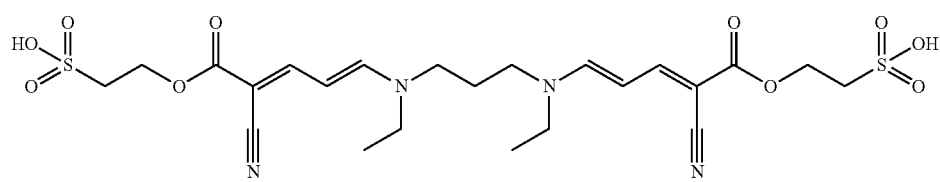
Among the compounds of formula (I) containing hydroxyl groups, the following compounds are novel:
(ab) 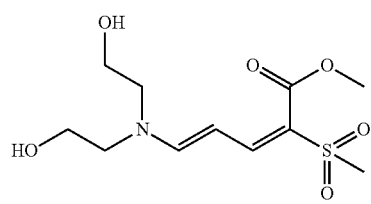
(ac) 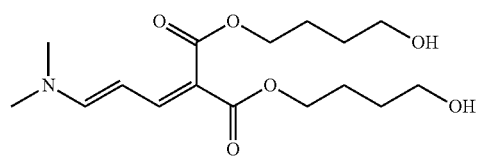
(ad) 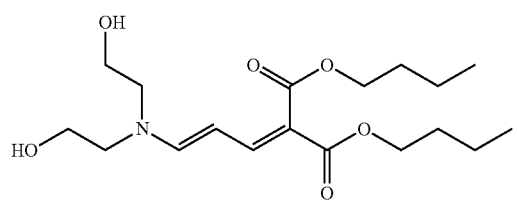
(ae) 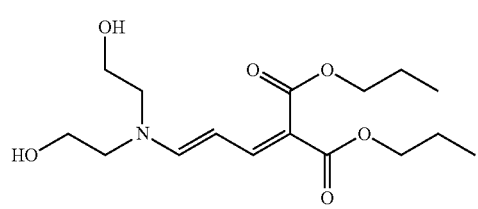
(af) 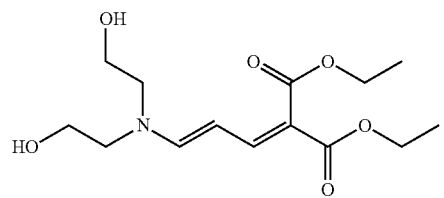
(ah) 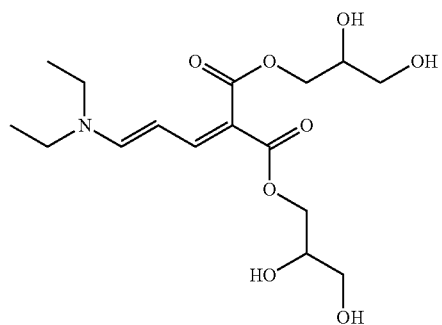
The compounds of formula (II) are novel, in particular the following compounds:
(bg) 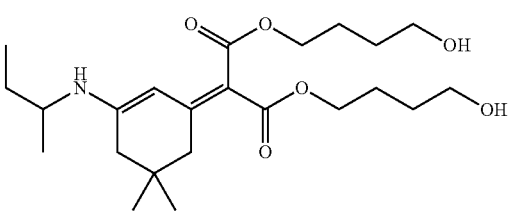
(bh) 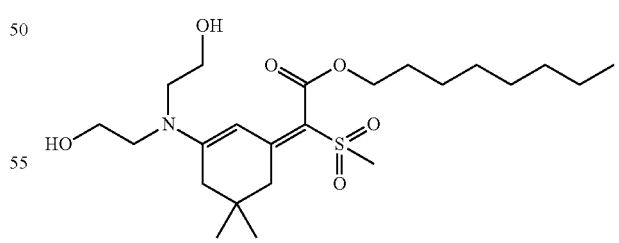
(bj) 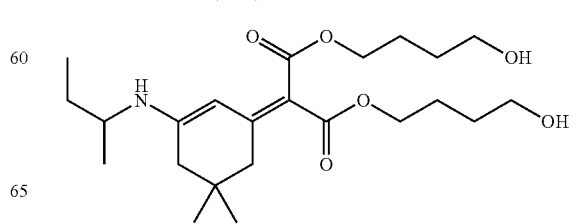

(bk)
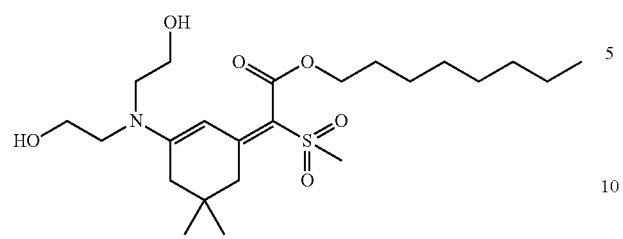
The following compounds are also novel:
(v)
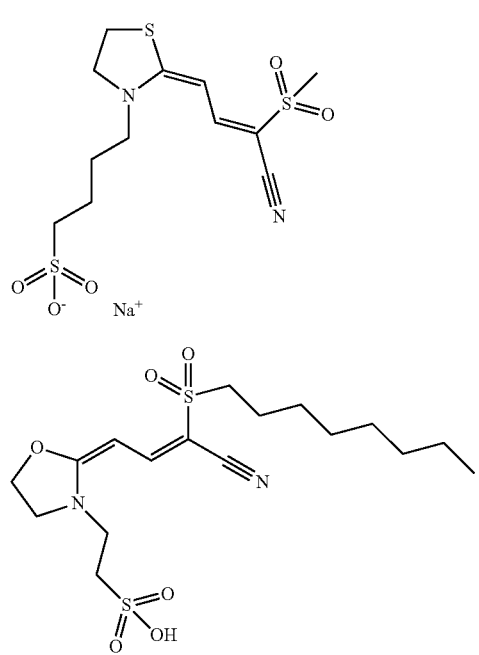
(w)
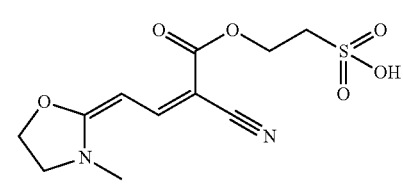
(x)
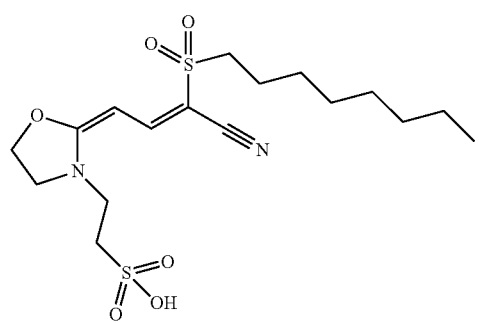
(z)
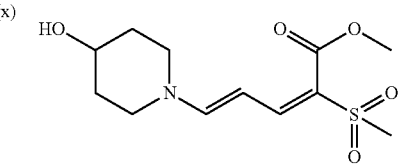
(ag)
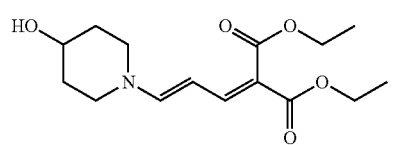
(ai)
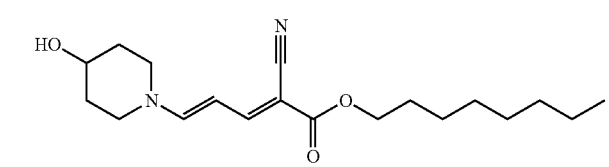
(aj)
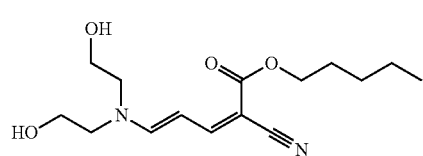
(ak)
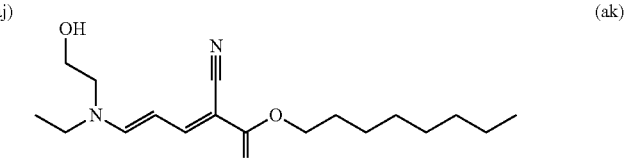
(al)
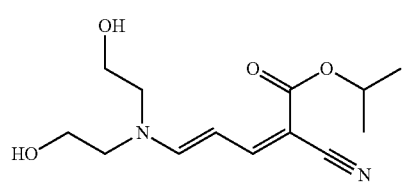
(am)
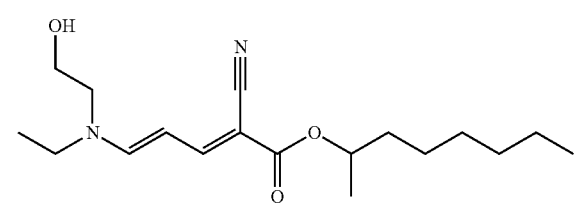

-continued
(an)
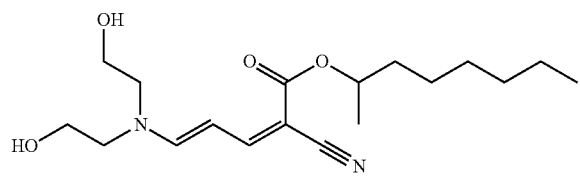
(ao)
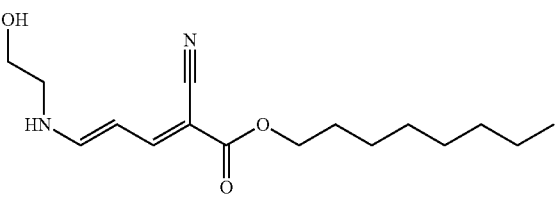
(ap)
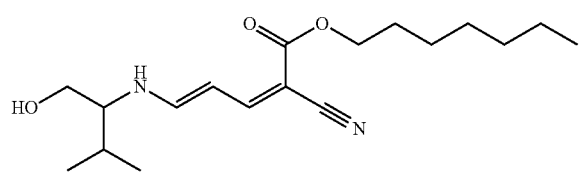
(aq)
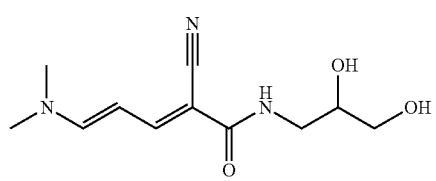
(ar)
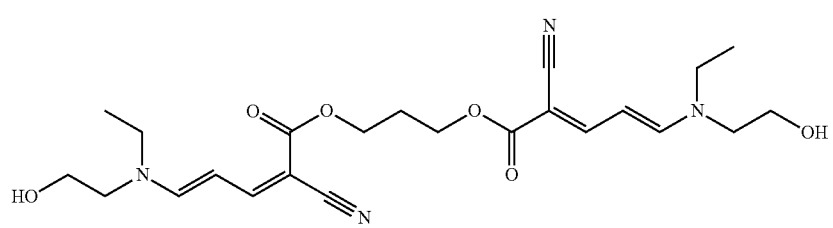
(as)
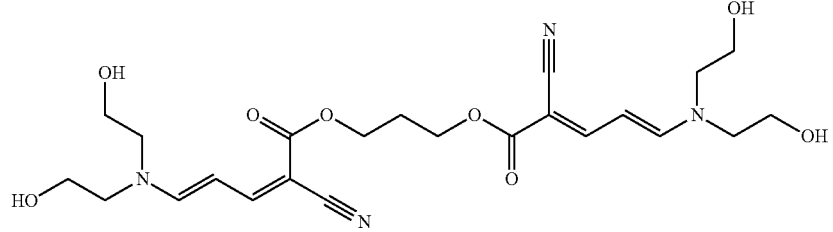
(at)
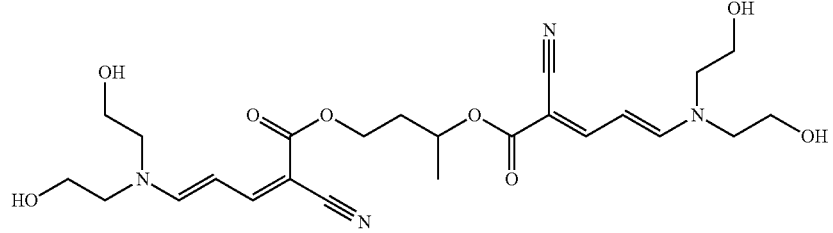
(au)
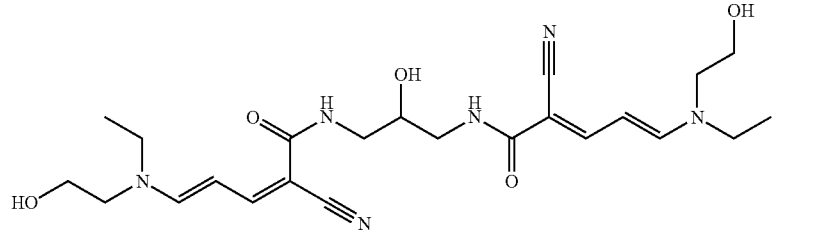
(av)
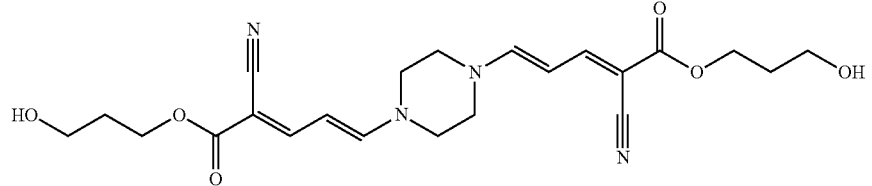

-continued
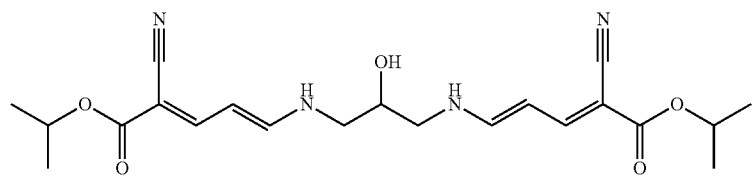 (aw)
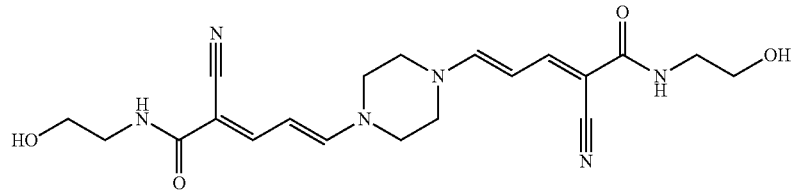 (ax)
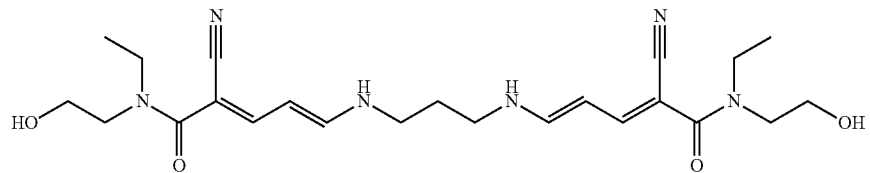 (ay)
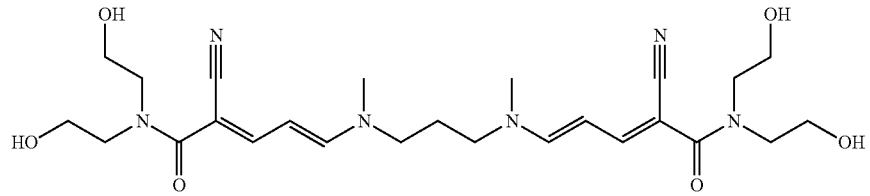 (az)
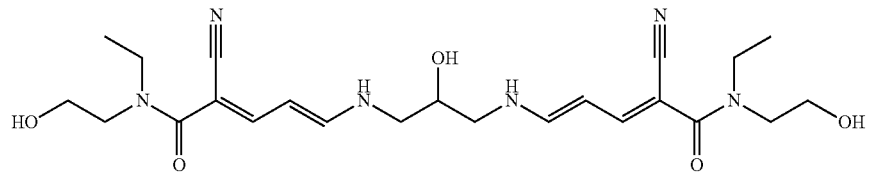 (ba)
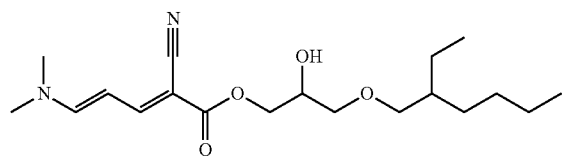 (bb)
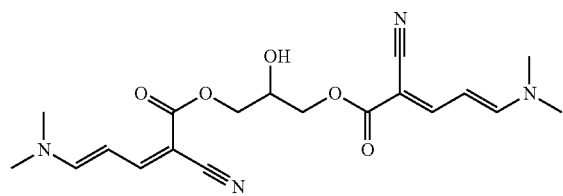 (bc)
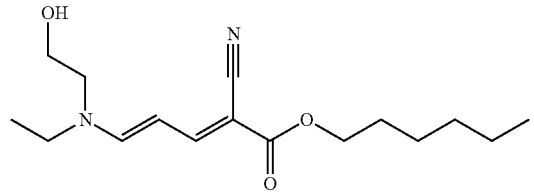 (bd)
(be)
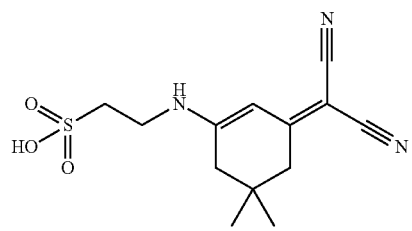 (bf)
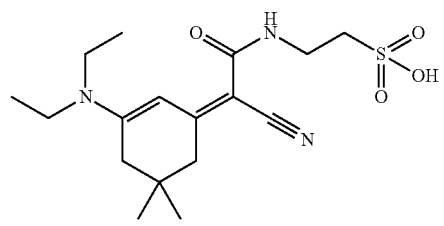 (bi)

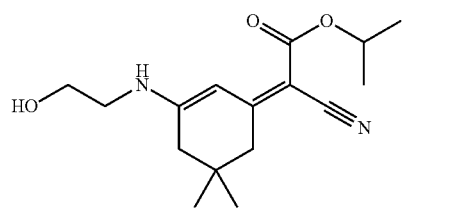
(bl)

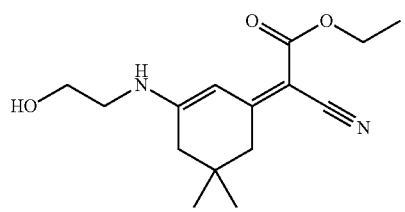
(bm)

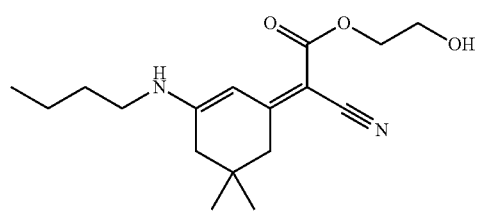
(bn)

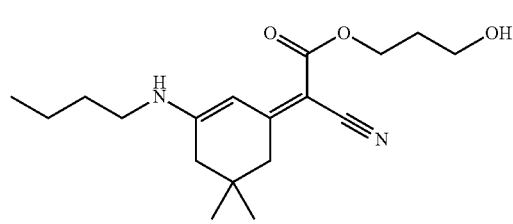
(bp)

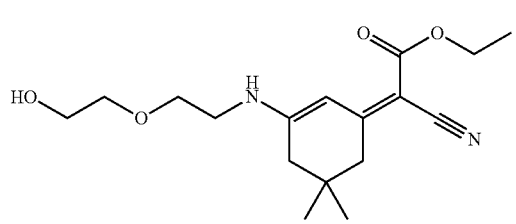
(bq)

(bo)

The hydrophilic or water-soluble merocyanin screening agent(s) in accordance with the invention may be present in the compositions according to the invention in a concentration of between 0.1% and 10% and preferably between 0.2% and 5% by weight relative to the total weight of the composition.

The compositions in accordance with the invention may also comprise other additional UVA-active and/or UVB-active organic or mineral UV-screening agents that are water-soluble or liposoluble or even insoluble in the cosmetic solvents commonly used.

Needless to say, a person skilled in the art will take care to select the optional additional screening agent(s) and/or the amounts thereof such that the advantageous properties intrinsically associated with the compositions in accordance with the invention are not, or are not substantially, adversely affected by the envisaged addition(s), especially the improvement in the photostability of the dibenzoylmethane derivative.

The additional organic screening agents are chosen especially from anthranilates; cinnamic derivatives; salicylic derivatives; camphor derivatives; benzophenone derivatives; β,βdiphenylacrylate derivatives; triazine derivatives other than those of formula (II); benzotriazole derivatives; benzalmalonate derivatives, especially those mentioned in U.S. Pat. No. 5,624,663; benzimidazole derivatives; imidazolines; bisbenzazolyl derivatives as described in patents EP 669 323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166, 355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; αalkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanin derivatives other than those of formula (I), such as those described in patent applications WO 04/006 878, WO 05/058 269 and WO 06/032 741; and mixtures thereof.

As examples of organic UV-screening agents, mention may be made of those denoted hereinbelow under their INCI name:

Para-aminobenzoic Acid Derivatives:
PABA,
Ethyl PABA,
Ethyl Dihydroxypropyl PABA,
Ethylhexyl dimethyl PABA sold in particular under the name Escalol 507 by ISP, Glyceryl PABA,
PEG-25 PABA sold under the name Uvinul P25 by BASF,
Salicylic Derivatives:
Homosalate sold under the name Eusolex HMS by Rona/EM Industries,
Ethylhexyl salicylate sold under the name Neo Heliopan OS by Symrise,
Dipropylene glycol salicylate sold under the name Dipsal by Scher,
TEA salicylate sold under the name Neo Heliopan TS by Sym rise,
Cinnamic Derivatives:
Ethylhexyl methoxycinnamate sold especially under the trade name Parsol MCX by DSM Nutritional Products,
Isopropyl methoxycinnamate,
Isoamyl methoxycinnamate sold under the trade name Neo Heliopan E 1000 by Symrise,
Cinoxate,
DEA Methoxycinnamate,
Diisopropyl methylcinnamate,
Glyceryl ethylhexanoate dimethoxycinnamate, β,β-Diphenylacrylate derivatives:
Octocrylene sold especially under the trade name Uvinul N539 by BASF,
Etocrylene sold especially under the trade name Uvinul N35 by BASF,
Benzophenone Derivatives:
Benzophenone-1 sold under the trade name Uvinul 400 by BASF,
Benzophenone-2 sold under the trade name Uvinul D50 by BASF,
Benzophenone-3 or Oxybenzone sold under the trade name Uvinul M40 by BASF,
Benzophenone-4 sold under the trade name Uvinul MS40 by BASF,
Benzophenone-5,
Benzophenone-6 sold under the trade name Helisorb 11 by Norquay,
Benzophenone-8 sold under the trade name Spectra-Sorb UV-24 by American Cyanamid,
Benzophenone-9 sold under the trade name Uvinul DS-49 by BASF,
Benzophenone-12,
n-hexyl 2-(4-diethylamino-2-hydroxybenzoyl)benzoate sold under the trade name Uvinul A+ or in the form of a mixture with octyl methoxycinnamate under the trade name Uvinul A+B by BASF,
1,1'-(1,4-piperazinediyl)bis[1-[2-[4-(diethylamino)-2-hydroxybenzoyl]phenyl]methanone (CAS 919803-06-8),
Benzylidenecamphor Derivatives:
3-Benzylidenecamphor manufactured under the name Mexoryl SD by Chimex,
4-Methylbenzylidenecamphor sold under the name Eusolex 6300 by Merck, Benzylidenecamphorsulfonic acid manufactured under the name Mexoryl SL by Chimex,
Camphor benzalkonium methosulfate manufactured under the name Mexoryl SO by Chimex,
Terephthalylidenedicamphorsulfonic acid manufactured under the name Mexoryl SX by Chimex,
Polyacrylamidomethylbenzylidenecamphor manufactured under the name Mexoryl SW by Chimex,
Phenylbenzimidazole Derivatives:
Phenylbenzimidazolesulfonic acid sold in particular under the trade name Eusolex 232 by Merck,
Disodium phenyl dibenzimidazole tetrasulfonate sold under the trade name Neo Heliopan AP by Symrise,
Phenylbenzotriazole Derivatives:
Drometrizole trisiloxane sold under the name Silatrizole by Rhodia Chimie, Methylenebis(benzotriazolyl)tetramethylbutylphenol sold in solid form under the trade name Mixxim BB/100 by Fairmount Chemical, or in micronized form as an aqueous dispersion under the trade name Tinosorb M by Ciba Specialty Chemicals,
Triazine Derivatives:
Bis(ethylhexyloxyphenol)methoxyphenyltriazine sold under the trade name Tinosorb S by Ciba Geigy,
Ethylhexyltriazone sold in particular under the trade name Uvinul T150 by BASF,
Diethylhexylbutamidotriazone sold under the trade name Uvasorb HEB by Sigma 3V,
2,4,6-Tris(diisobutyl 4'-aminobenzalmalonate)-s-triazine,
2,4,6-Tris(dineopentyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)oxy]-disiloxanylpropyl)amino]-s-triazine,
the symmetrical triazine screening agents described in U.S. Pat. No. 6,225,467, patent application WO 2004/085 412 (see compounds 6 and 9) or the document Symmetrical Triazine Derivatives IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in Beiersdorf patent applications WO 06/035 000, WO 06/034 982, WO 06/034 991, WO 06/035 007, WO 2006/034 992 and WO 2006/034 985,
Anthranilic Derivatives:
Menthyl anthranilate sold under the trade name Neo Heliopan MA by Symrise,
Imidazoline Derivatives:
Ethylhexyldimethoxybenzylidenedioxoimidazoline propionate,
Benzalmalonate Derivatives:
Dineopentyl 4'-methoxybenzalmalonate
Polyorganosiloxane containing benzalmalonate functions, for instance
Polysilicone-15, sold under the trade name Parsol SLX by Hoffmann LaRoche,
4,4-Diarylbutadiene Derivatives:
1,1-Dicarboxy(2,2'-dimethylpropyl)-4,4-diphenyl-butadiene,
Benzoxazole Derivatives:
2,4-bis[5-1(dimethylpropyl)benzoxazol-2-yl-(4-phenyl)imino]-6-(2-ethylhexyl)imino-1,3,5-triazine, sold under the name of Uvasorb $K_2A$ by Sigma 3V,
and mixtures thereof.
The preferential additional organic screening agents are chosen from:
Ethylhexyl methoxycinnamate,
Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)-benzoate,
1,1'-(1,4-piperazinediyl)bis[14244-(diethylamino)-2-hydroxybenzoyl]phenyl}methanone,
4-Methylbenzylidenecamphor,
Terephthalylidenedicamphorsulfonic acid,
Disodium phenyldibenzimidazoletetrasulfonate,
Ethylhexyl triazone,
Bis(ethylhexyloxyphenol)methoxyphenyltriazine,
Diethylhexylbutamidotriazone,
2,4,6-Tris(biphenyl-4-yl)-1,3,5-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)oxy]-disiloxanylpropyl)amino]-s-triazine,
Methylenebis(benzotriazolyl)tetramethylbutylphenol,
Drometrizole trisiloxane,
Polysilicone-15,
Dineopentyl 4'-methoxybenzalmalonate
1,1-Dicarboxy(2,2'-dimethylpropyl)-4,4-diphenyl-butadiene,
2,4-Bis[5-1(dimethylpropyl)benzoxazol-2-yl-(4-phenyl)imino]-6-(2-ethylhexyl)imino-1,3,5-triazine,
and mixtures thereof.

The additional mineral screening agents are chosen from coated or uncoated metal oxide pigments, for instance pigments of titanium oxide (amorphous or crystallized in rutile and/or anatase form), iron oxide, zinc oxide, zirconium oxide or cerium oxide, which are all UV-photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (of titanium or of aluminium), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkyl silanes.

The silicones used for coating the nanopigments that are suitable for the present invention are preferably chosen from the group containing alkyl silanes, polydialkylsiloxanes and polyalkylhydrogenosiloxanes. Even more preferentially, the silicones are chosen from the group containing octyltrimethylsilane, polydimethylsiloxanes and polymethylhydrogenosiloxanes.

Needless to say, before being treated with silicones, the metal oxide pigments may have been treated with other surface agents, in particular with cerium oxide, alumina, silica, aluminium compounds or silicon compounds, or mixtures thereof.

The coated pigments are, for example, titanium oxides that have been coated:

with silica, such as the product Sunveil from the company Ikeda and the product Eusolex T-AVO from the company Merck, with silica and iron oxide, such as the product Sunveil F from the company Ikeda, with silica and alumina, such as the products Microtitanium Dioxide MT 500 SA and Microtitanium Dioxide MT 100 SA from the company Tayca, Tioveil from the company Tioxide and Mirasun TiW 60 from the company Rhodia, with alumina, such as the products Tipaque TTO-55 (B) and Tipaque TTO-55 (A) from the company Ishihara and UVT 14/4 from the company Kemira, with alumina and aluminium stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Uniqema, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, or the product SMT-100 WRS from the company Tayca, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

Other titanium oxide pigments treated with a silicone are, for example, $TiO_2$ treated with octyltrimethylsilane, such as the product sold under the trade name T 805 by the company Degussa Silicas, $TiO_2$ treated with a polydimethylsiloxane, such as the product sold under the trade name 70250 Cardre UF TiO2SI3 by the company Cardre, anatase/rutile $TiO_2$ treated with a polydimethylhydrogenosiloxane, such as the product sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wacker under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:
 those sold under the name Z-Cote by the company Sunsmart;
 those sold under the name Nanox by the company Elementis;
 those sold under the name Nanogard WCD 2025 by the company Nanophase Technologies.

The coated zinc oxide pigments are, for example:
 those sold under the name Z-Cote HP1 by the company Sunsmart (dimethicone-coated ZnO);
 those sold under the name Zinc Oxide CS-5 by the company Toshibi (ZnO coated with polymethylhydrogenosiloxane);
 those sold under the name Nanogard Zinc Oxide FN by the company Nanophase Technologies (as a 40% dispersion in Finsolv TN, C12-C15 alkyl benzoate);
 those sold under the name Daitopersion ZN-30 and Daitopersion ZN-50 by the company Daito (dispersions in cyclopolymethylsiloxane/oxyethylenated polydimethylsiloxane, containing 30% or 50% of nanozinc oxides coated with silica and polymethylhydrogenosiloxane);
 those sold under the name NFD Ultrafine ZnO by the company Daikin (ZnO coated with perfluoroalkyl phosphate and copolymer based on perfluoroalkylethyl as a dispersion in cyclopentasiloxane);
 those sold under the name SPD-Z1 by the company Shin-Etsu (ZnO coated with silicone-grafted acrylic polymer, dispersed in cyclodimethylsiloxane);

those sold under the name Escalol Z100 by the company ISP (alumina-treated ZnO dispersed in an ethylhexyl methoxycinnamate/PVP-hexadecene/methicone copolymer mixture);

those sold under the name Fuji ZnO-SMS-10 by the company Fuji Pigment (ZnO coated with silica and polymethylsilsesquioxane);

those sold under the name Nanox Gel TN by the company Elementis (ZnO dispersed at a concentration of 55% in C12-C15 alkyl benzoate with hydroxystearic acid polycondensate).

The uncoated cerium oxide pigments are sold, for example, under the name Colloidal Cerium Oxide by the company Rhône-Poulenc.

The uncoated iron oxide nanopigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220, The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, especially of titanium dioxide and of cerium dioxide, including the silica-coated equal-weight mixture of titanium dioxide and of cerium dioxide, sold by the company Ikeda under the name Sunveil A, and also the alumina, silica and silicone-coated mixture of titanium dioxide and of zinc dioxide, such as the product M 261 sold by the company Kemira, or the alumina, silica and glycerol-coated mixture of titanium dioxide and of zinc dioxide, such as the product M 211 sold by the company Kemira.

The additional UV-screening agents are generally present in the compositions according to the invention in proportions ranging from 0.01% to 20% by weight relative to the total weight of the composition, and preferably ranging from 0.1% to 10% by weight relative to the total weight of the composition.

The compositions in accordance with the present invention may also comprise standard cosmetic adjuvants chosen especially from oils, waxes, organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology.

Oils that may be mentioned include mineral oils (paraffin); plant oils (sweet almond oil, macadamia oil, blackcurrant seed oil or jojoba oil); synthetic oils, for instance perhydrosqualene, fatty alcohols, fatty amides (for instance isopropyl lauroyl sarcosinate sold under the name Eldew SL-205 by the company Ajinomoto), fatty acids or fatty esters, for instance the C12-C15 alkyl benzoate sold under the trade name Finsolv TN or Witconol TN by the company Witco, 2-ethylphenyl benzoate, for instance the commercial product sold under the name X-Tend 226® by the company ISP, octyl palmitate, isopropyl lanolate and triglycerides, including capric/caprylic acid triglycerides, and dicaprylyl carbonate sold under the name Cetiol CC by the company Cognis, oxyethylenated or oxypropylenated fatty esters and ethers; silicone oils (cyclomethicone and polydimethylsiloxanes, or PDMS) or fluoro oils, polyalkylenes, and trialkyl trimellitates such as tridecyl trimellitate.

Examples of waxy compounds that may be mentioned include carnauba wax, beeswax, hydrogenated castor oil, polyethylene waxes and polymethylene waxes, for instance the product sold under the name Cirebelle 303 by the company Sasol.

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

Hydrophilic thickeners that may be mentioned include carboxyvinyl polymers, such as Carbopols (Carbomers) and the Pemulens (acrylate/C10-C30-alkyl acrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS (CTFA name: ammonium polyacryloyldimethyl taurate or Simulgel 800 sold by the company SEPPIC (CTFA name: sodium polyacryolyldimethyltaurate/ polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethylcellulose; polysaccharides and especially gums such as xanthan gum; water-soluble or water-dispersible silicone derivatives, for instance acrylic silicones, polyether silicones and cationic silicones, and mixtures thereof.

Lipophilic thickeners that may be mentioned include synthetic polymers, such as the poly(C10-C30 alkyl acrylates) sold under the names Intelimer IPA 13-1 and Intelimer IPA 13-6 by Landec, or modified clays, such as hectorite and its derivatives, for instance the products sold under the name Bentone.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s), especially the improvement in the photostability of the dibenzoylmethane derivative.

The compositions according to the invention may be prepared according to the techniques that are well known to those skilled in the art. They may in particular be in the form of a simple or complex emulsion (O/W, W/O, 0/W/0 or W/O/W) such as a cream, a milk or a cream-gel; in the form of an aqueous gel; in the form of a lotion. They may optionally be packaged as an aerosol and may be in the form of a mousse or a spray.

The compositions according to the invention are preferably in the form of an oil-in-water or water-in-oil emulsion.

The emulsification processes that may be used are of paddle or impeller, rotor-stator and high-pressure homogenizer (HPH) type.

It is also possible, via HPH (between 50 and 800 bar), to obtain stable dispersions with drop sizes that may be as small as 100 nm.

The emulsions generally contain at least one emulsifying surfactant chosen from so amphoteric, anionic, cationic and nonionic emulsifying surfactants, which are used alone or as a mixture. The emulsifiers are appropriately chosen according to the emulsion to be obtained (W/O or O/W).

As emulsifying surfactants that may be used for the preparation of the W/0 emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE 09 by the company Goldschmidt. One or more co-emulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name Arlacel P135 by the company ICI.

Glycerol and/or sorbitan esters that may especially be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkyl-enated (oxyethylenated and/or oxypropylenated) fatty acid esters, for instance the mixture PEG-100 stearate/glyceryl stearate sold, for example, by the company ICI under the name Arlacel 165; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to a specific embodiment of the invention, the mixture of the alkyl polyglucoside as defined above with the corresponding fatty alcohol can be in the form of a self-emulsifying composition, for example as disclosed in the document WO-A-92/06778.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above for the manufacture of cosmetic products for treating the skin, the lips, the nails, the hair, the eyelashes, the eyebrows and/or the scalp, especially care products, antisun products and makeup products.

The cosmetic compositions according to the invention may be used, for example, as makeup products.

The cosmetic compositions according to the invention may be used, for example, as care products and/or antisun protection products for the face and/or the body, of liquid to semi-liquid consistency, such as milks, more or less rich creams, cream-gels and pastes. They may optionally be packaged as an aerosol and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in U.S. Pat. Nos. 4,077,441 and 4,850,517 (which form an integral part of the content of the description).

The compositions conditioned in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions according to the invention may also comprise additional cosmetic or dermatological active agents.

Mention may be made, among active agents, of:
vitamins (A, C, E, K, PP, and the like) and their derivatives or precursors, alone or as mixtures;
anti-ageing agents;
antioxidants;
free-radical scavengers;
antiglycation agents;
calmatives;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
dermorelaxants;
tensioning agents;
matting agents;
keratolytic agents;
desquamating agents;
moisturizers, for instance polyols such as glycerol, butylene glycol or propylene glycol;
antiinflammatory agents;
agents that act on the energy metabolism of cells;
insect repellents;
substance P or substance CRGP antagonists;
hair-loss counteractants and/or hair restorers;
antiwrinkle agents;
agents for modifying skin pigmentation;
astringents;
seboregulators and antiseborrhoeic agents.

Needless to say, a person skilled in the art will take care to select the optional additional compound(s) and/or the amounts thereof such that the advantageous properties intrinsically associated with the compositions in accordance with the invention are not, or are not substantially, adversely affected by the envisaged addition(s).

A person skilled in the art will select the said active agent(s) as a function of the effect desired on the skin, the hair, the eyelashes, the eyebrows and the nails.

The composition may also comprise at least one ingredient such as fillers with a soft-focus effect or agents for promoting the natural coloration of the skin, intended for complementing the biological effects of these active agents or for providing an immediate visual anti-ageing effect.

Other Additional Ingredients

The composition may also comprise at least one additional ingredient intended to provide an immediate visual effect. Mention may be made especially of agents that promotes the naturally pinkish coloration of the skin.

As agents that promote the naturally pinkish coloration of the skin, examples that may be mentioned include self-tanning agents, for instance an agent which, when applied to the skin, especially to the face, makes it possible to obtain a tanning effect more or less similar in appearance to that which may result from prolonged exposure to sunlight (natural tanning) or under a UV lamp.

Examples of self-tanning agents that may especially be mentioned include:
dihydroxyacetone (DHA),
erythrulose, and
the combination of a catalytic system formed from:
manganese and/or zinc oxide salts, and
alkali metal and/or alkaline-earth metal hydrogen carbonates.

The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in patent application FR 2 466 492 and WO 97/35842, dihydroxyacetone (DHA) and 4,4-dihydroxypyrazolin-5-one derivatives as described in patent application EP 903 342. DHA will preferably be used.

The DHA may be used in free and/or encapsulated form, for example in lipid vesicles such as liposomes, especially described in patent application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluorane type such as those described in patent application FR 2 840 806. Mention may be made, for example, of the following dyes:

tetrabromofluoresceine or eosin known under the CTFA name: CI-45380 or Red 21
phloxin B known under the CTFA name: CI-45410 or Red 27
diiodofluoresceine known under the CTFA name: CI-45425 or Orange 10;
dibromofluoresceine known under the CTFA name: CI-45370 or Orange 5;
the sodium salt of tetrabromofluoresceine known under the CTFA name: CI-45380 (Na salt) or Red 22;
the sodium salt of phloxin B known under the CTFA name: CI-45410 (Na salt) or Red 28;
the sodium salt of diiodofluoresceine known under the CTFA name: CI-45425 (Na salt) or Orange 11;
erythrosine known under the CTFA name: CI-45430 or Acid Red 51.
phloxin known under the CTFA name: CI-45405 or Acid Red 98.

These dyes may also be chosen from anthraquinones, caramel, carmine, carbon black, azulene blues, methoxalene, trioxalene, guajazulene, chamuzulene, rose Bengal, eosin 10B, cyanosin and daphinin.

These dyes may also be chosen from indole derivatives, for instance the monohydroxyindoles as described in patent FR 2 651 126 (i.e.: 4-, 5-, 6- or 7-hyfroxyindole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

EXAMPLES OF SYNTHESIS

Example 1

Preparation of methyl (2Z,4E)-5-[bis(2-hydroxyethyl)amino]-2-(methylsulfonyl)penta-2,4-dienoate

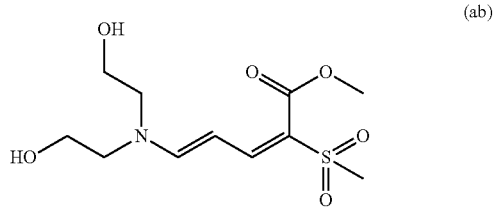 [SMILES: COC(=O)/C(=C\C=C\N(CCO)CCO)S(C)(=O)=O]

(ab)

First Step: Preparation of methyl(2Z,4E)-5-[acetyl(phenyl)amino]-2-(methylsulfonyl)penta-2,4-dienoate 3-Anilinoacrolein aniline (2 g, $9 \times 10^{-3}$ mol) and methylmethanesulfonyl acetate (1.37 ml, $9 \times 10^{-3}$ mol) are heated at 105° C. in 5 ml of acetic anhydride for 2 hours 30 minutes. After cooling, the acetic anhydride is evaporated off under vacuum. The brown solid obtained is taken up in 40 ml of methanol and brought to reflux. After cooling, the solid obtained is filtered off, rinsed with cold methanol and dried. 1.6 g of a yellow powder (yield: 55%) of methyl (2Z,4E)-5-[acetyl(phenyl)amino]-2-(methylsulfonyl)penta-2,4-dienoate are recovered and are used in the following step without further processing.

Second Step: Preparation of the Compound of Example 1

A solution of the preceding product (2.3 g, $7.1 \times 10^{-3}$ mol) and of diethanolamine (10.33 g, $6.23 \times 10^{-3}$ mol) in 5.5 ml of acetonitrile is refluxed for 1 hour 15 minutes. After cooling, the acetonitrile is evaporated off under vacuum. The brown oil obtained is chromatographed on a column of silica (gradient of eluents: CH2Cl2/MeOH 100:0 to 90:10). 0.36 g (yield: 26%) of clean fractions of the derivative of Example 1 is thus obtained in the form of a pale yellow powder:

m.p: 73-76° C.

UV (Ethanol): $\lambda_{max}$=367 nm, $E_{1\%}$=2140

Example 2

Preparation of bis(4-hydroxybutyl) [(2E)-3-(dimethylamino)prop-2-en-1-ylidene]propanedioate

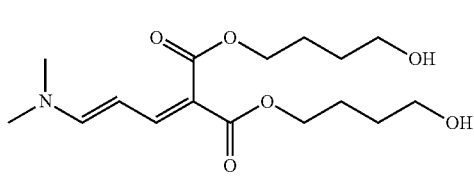

(ac)

First Step: Preparation of bis[4-(benzyloxy)butyl]propanedioate

A heterogeneous mixture of 4-benzyloxy-1-butanol (9.5 g, 52.8×10⁻³ mol) and of malonic acid (2.5 ml, 24×10⁻³ mol) is brought to 50° C. with stirring. The catalyst concentrated $H_2SO_4$ (131 μL) is added, and the resulting mixture is left at 40° C. for 1 hour. After cooling, the grey residue is taken up in dichloromethane. The organic phase is washed with water (abundant foam). After evaporating off the solvent, the residue obtained is chromatographed on a column of silica to remove the starting alcohol (eluent: 90/10 heptane/EtOAc). 7.5 g (yield: 74%) of clean fractions of bis[4-(benzyloxy)butyl]propanedioate are recovered in the form of a pale yellow oil and are used in the following step without further processing.

Second Step: Preparation of bis(4-hydroxybutyl)propanedioate

The preceding product (7.5 g, 0.0175 mol) dissolved in 350 ml of ethanol was subjected to continuous reductive hydrogenation (H-cube: 70 mm cartridge of 10% Pd on C; Full H2; 1 ml/min; 40° C.). After distilling off the ethanol under vacuum, 4.31 g (yield: 99%) of bis(4-hydroxybutyl) propanedioate are obtained in the form of a colourless oil and are used in the following step without further processing.

Third Step: Preparation of the Compound of Example 2

The preceding product (4.31 g, 0.0173 mol) and the catalysts n-octylamine (86 μL, 0.03 eq.) and acetic acid (199 μL, 0.2 eq.) in 20 ml of toluene are brought to reflux in a reactor inertized with nitrogen and on which is mounted Dean-Stark apparatus. N,N-Dimethylacrolein (1.74 ml, 0.0173 mol) dissolved in 10 ml of toluene is added dropwise to the reaction mixture. After boiling the reaction mixture for 3 hours 30 minutes, the same amounts of catalyst are added and refluxing is continued for 21 hours. After cooling, the solvent is evaporated off under vacuum and the brown oil obtained is chromatographed on a column of silica (gradient of eluents: isopropyl ether/acetone from 30:70 to 70:30). 703 mg (yield: 12%) of the derivative of Example 2 are thus obtained in the form of an orange-coloured oil:

UV (Ethanol): $\lambda_{max}$=374 nm, $E_{1\%}$=1600

Example 3

Preparation of 2-{[(2E,4E)-2-cyano-5-(diethylamino)penta-2,4-dienoyl]oxy}ethanesulfonate sodium salt

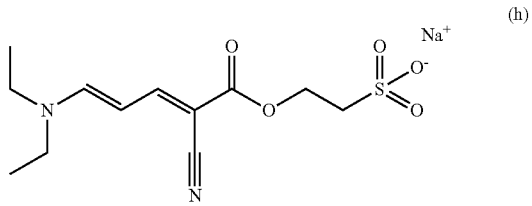 [SMILES: [Na+] ; CCN(/C=C/C=C(\C#N)C(=O)OCCS(=O)(=O)[O-])CC]

(h)

First Step: Preparation of sodium 2-{[(2E,4E)-2-cyano-5-(diethylamino)penta-2,4-dienoyl]oxy}ethanesulfonate Thionyl chloride (15 ml) is reacted, with stirring, with cyanoacetic acid (2 g, 0.024 mol) and maintained at 40° C. for 2 hours. 50 ml of toluene are added and the mixture is concentrated under vacuum until a residual volume of 10 ml is obtained. The sodium salt of isethionic acid (3.48 g, 0.024 mol) is added thereto and the mixture is maintained at the reflux point of the toluene. The heterogeneous mixture is refluxed for 20 hours. After cooling, the reaction mixture is filtered. The solid is taken up in water and the aqueous phase is washed with ethyl acetate. The aqueous phase is brought to neutral pH with 2N sodium hydroxide. 1.6 g of a beige-coloured powder containing about 30% by mass of salts are recovered. The sodium salt of 2-{[(2E,4E)-2-cyano-5-(diethylamino)penta-2,4-dienoyl]oxy}ethanesulfonic acid is thus obtained, and is used in the following step without further processing.

Second Step: Preparation of the Compound of Example 3

The preceding product (1 g, 0.0032 mol) and the catalysts diethylamine (34 μL, 0.1 eq.) and acetic acid (19 μL, 0.1 eq.) in 5 ml of toluene are brought to reflux in a reactor inertized with nitrogen and on which is mounted Dean-Stark apparatus. N,N-Diethylacrolein (0.41 ml, 0.0032 mol) is added dropwise to the reaction mixture. After boiling the reaction mixture for 3 hours 30 minutes, the same amounts of catalyst are added and refluxing is continued for 21 hours. After cooling, the reaction mixture is filtered and the solid obtained is washed with diisopropyl ether. After chromatography on a reverse-phase column, 212 mg (yield: 22%) of the derivative of Example 3 are obtained in the form of a beige-coloured solid:

UV ($H_2O$): $\lambda_{max}$=370 nm, $E_{1\%}$=1200

III/Formulation Examples

Compositions A and B were prepared:

| Ingredients | Ex. A | Ex. B |
|---|---|---|
| EDTA | 0.1 | 0.1 |
| Monopotassium monocetyl phosphate | 1 | 1 |

-continued

| Ingredients | Ex. A | Ex. B |
|---|---|---|
| Deionized water | qs 100 | qs 100 |
| Triethanolamine | 0.3 | 0.3 |
| Preserving agents | 1.2 | 1.2 |
| $C_{12}$-$C_{15}$ alkyl benzoate | 20 | 20 |
| Preserving agents | 0.25 | 0.25 |
| Stearic acid | 1.5 | 1.5 |
| Glyceryl mono/distearate/polyethylene glycol stearate (100 EO) mixture | 1 | 1 |
| Cetyl alcohol | 0.5 | 0.5 |
| Cetearyl alcohol and cetearyl glucoside | 2 | 2 |
| Dimethicone (350 cSt) | 0.5 | 0.5 |
| Triethanolamine | 0.45 | 0.45 |
| Drometrizole trisiloxane | 2 | 2 |
| Avobenzone (Parsol 1789) | 2 | 2 |
| Merocyanin of formula (y) | 1.5 | 0 |
| Merocyanin of formula (ac) | 0 | 1.5 |
| 2,4,6-tris[p-(2'-ethylhexyl-1'-oxycarbonyl)anilino]-1,3,5-triazine | 2 | 2 |
| Isohexadecane | 1 | 1 |
| Copolymer of acrylic acid and of C10-C30 alkyl methacrylate | 0.2 | 0.2 |
| Xanthan | 0.2 | 0.2 |
| Cyclopentadimethylsiloxane | 5 | 5 |

The invention claimed is:

1. A composition comprising, in a cosmetically acceptable support, at least one UV-screening system, characterized in that it comprises:
   (a) at least one dibenzoylmethane derivative and
   (b) at least one hydrophilic or water-soluble merocyanin UV-screening agent,
   wherein the hydrophilic or water-soluble merocyanin UV screening agent(s) is the following compound (ac), a salt thereof or the E,E, Z,Z, E,Z isomer forms thereof:

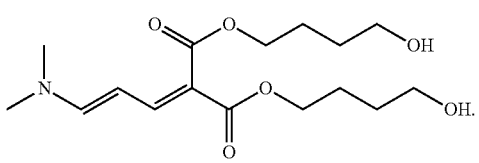

(ac)

2. Composition according to claim 1, in which the dibenzoylmethane derivative is 4-(tert-butyl)-4'-methoxydibenzoylmethane, or Butyl Methoxy Dibenzoylmethane or Avobenzone, having the following formula:

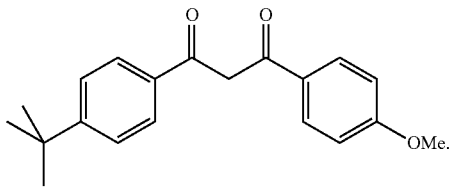 [SMILES: COc1ccc(C(=O)CC(=O)c2ccc(C(C)(C)C)cc2)cc1]

3. Composition according to claim 1, wherein it also contains other UVA-active and/or UVB-active organic or mineral screening agents, which are water-soluble or liposoluble, or else insoluble in the commonly used cosmetic solvents.

4. Composition according to claim 3, in which the additional organic screening agents are chosen from anthranilates; cinnamic derivatives; salicylic derivatives; camphor derivatives; benzophenone derivatives; β, β-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; α-alkylstyrene-based dimers; 4,4-diarylbutadienes; liposoluble merocyanin derivatives; and mixtures thereof.

5. Composition according to claim 4, wherein the organic UV-screening agent(s) are chosen from the following compounds:
Ethylhexyl methoxycinnamate,
Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)-benzoate,
1,1'-(1,4-Piperazinediyl)bis[1-[2-[4-(diethylamino)-2-hydroxybenzoyl]phenyl]methanone, 4-Methylbenzylidenecamphor,
Terephthalylidenedicamphorsulfonic acid,
Disodium phenyldibenzimidazoletetrasulfonate,
Ethylhexyl triazone,
Bis(ethylhexyloxyphenol)methoxyphenyltriazine,
Diethylhexylbutamidotriazone,
2,4,6-Tris(biphenyl-4-yl)-1,3,5-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-[(3-{1,3,3,3-tetramethyl-1-[(trimethylsilyl)oxy]-disiloxanylpropyl) amino]-s-triazine,
Methylenebis(benzotriazolyl)tetramethylbutylphenol,
Drometrizole trisiloxane,
Polysilicone-15,
Dineopentyl 4'-methoxybenzalmalonate,
1,1-Dicarboxy(2,2'-dimethylpropyl)-4,4-diphenyl-butadiene,
2,4-Bis[5-1(dimethylpropyl)benzoxazol-2-yl-(4-phenyl) imino]-6-(2-ethylhexyl)imino-1,3,5-triazine,
and mixtures thereof.

6. Composition according to claim 3, wherein the additional mineral screening agents are coated or uncoated metal oxide pigments.

* * * * *